United States Patent [19]
Nesvadba

[11] Patent Number: 5,190,999
[45] Date of Patent: Mar. 2, 1993

[54] α-CARBONYLPHENYLACETONITRILE DERIVATIVES AS STABILIZERS FOR ORGANIC MATERIALS

[75] Inventor: Peter Nesvadba, Marly, Switzerland

[73] Assignee: Ciba-Geigy Corporation, Ardsley, N.Y.

[21] Appl. No.: 719,860

[22] Filed: Jun. 24, 1991

[30] Foreign Application Priority Data

Jun. 28, 1990 [CH] Switzerland .................. 2160/90

[51] Int. Cl.$^5$ .................. C08K 5/5353; C08K 5/26; C08K 5/16; C07C 309/06; C07C 213/57; C07C 243/28; C07C 255/40; C07C 255/44; C07C 255/41
[52] U.S. Cl. .................. 524/96; 252/49.9; 252/51.5 R; 524/99; 524/100; 524/111; 524/205; 524/206; 524/207; 524/208; 524/209; 544/163; 544/226; 544/386; 548/538; 549/496; 558/154; 558/168; 558/404; 558/405; 558/406; 558/386
[58] Field of Search .................. 524/205, 206, 207, 208, 524/209, 111, 96, 100, 99, 124; 558/404, 405, 406, 154, 168, 386; 549/496; 548/538; 544/226, 386, 163; 252/49.9, 51.5 R

[56] References Cited

U.S. PATENT DOCUMENTS

| | | |
|---|---|---|
| 2,297,911 | 10/1942 | Niederl .................. 558/406 |
| 2,440,421 | 4/1948 | Wallingford et al. .................. 558/406 |
| 3,089,860 | 5/1963 | Baum et al. . |
| 3,310,555 | 3/1967 | Pesson . |
| 3,344,023 | 9/1967 | Reinhold et al. . |
| 3,585,234 | 6/1971 | Yoshioka et al. .................. 558/406 |
| 3,721,704 | 3/1973 | Dexter .................. 558/406 |
| 3,726,837 | 4/1973 | de Jongh et al. . |
| 3,793,364 | 2/1974 | Patmore . |
| 3,945,896 | 3/1976 | Tyssee .................. 558/406 |
| 3,984,460 | 10/1976 | Spivack . |
| 4,049,713 | 9/1977 | Spivack . |
| 4,093,587 | 6/1978 | Spivack . |
| 4,469,688 | 9/1984 | D'Silva .................. 558/168 |
| 4,740,228 | 4/1988 | Kis-Tamas et al. .................. 558/404 |
| 4,894,472 | 1/1990 | Seng et al. .................. 558/406 |

FOREIGN PATENT DOCUMENTS 0333643 9/1989 European Pat. Off. .
58-201851 11/1983 Japan .
573386 3/1976 Switzerland .

OTHER PUBLICATIONS

Chemical Abstracts 43, 2269e (1949).
H. A. P. de Jongh et al., J. Org. Chem. 36, 3160 (1971).
R. Metze et al., Chem. Ber. 91, 1798 (1958).
Chem. Abst. 87, 184219d (1977).
Chem. Abst. 91, 39426x.
Chem. Abst. 94, 151882f (1981).
Chem. Abst. 97, 87060u (1982).
Chem. Abst. 98, 138991d (1983).
Chem. Abst. 100, 51289s (1984).
Chem. Abst. 103, 18295e (1985).
Chem. Abst. 103, 215070d (1985).
Chem. Abst. 104, 224795s.
Chem. Abst. 106, 63041s (1987).
Chem. Abst. 109, 92273m (1989).
Chem. Abst. 110, 90027f (1989).
Chem. Abst. 110, 154213y (1989).

Primary Examiner—Veronica P. Hoke
Attorney, Agent, or Firm—Luther A. R. Hall

[57] ABSTRACT

Compositions comprising an organic material liable to oxidative, thermal and/or actinic degradation and at least one compound of the formula I

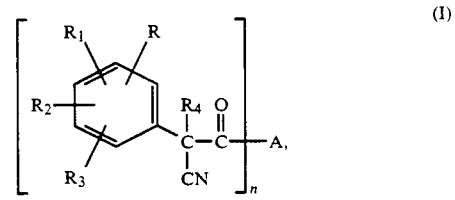

are described in which n is 1-6, R, $R_1$, $R_2$, $R_3$ and $R_4$ are preferably hydrogen and A is a monovalent radical or polyvalent linking moiety.

Some of the compounds of the formula I are novel. They are particularly suitable for the stabilization of lubricating oils, metal processing fluids and hydraulic fluids, and of thermoplastics and elastomers.

20 Claims, No Drawings

α-CARBONYLPHENYLACETONITRILE DERIVATIVES AS STABILIZERS FOR ORGANIC MATERIALS

The present invention relates to compositions comprising an organic material liable to oxidative, thermal and/or actinic degradation and at least one α-carbonylphenylacetonitrile compound. The invention further relates to the use of these compounds as additives for the stabilisation of organic material and to new α-carbonylphenylacetonitrile derivatives.

JP-A 58-201851 discloses that chlorine-containing polymers can be stabilised by mixtures of organometallic Ba, Ca, Mg, Sr, Li, K, Na, Zn and/or Sn compounds, for example metal soaps of saturated or unsaturated mono- or dicarboxylates of this type having 6–22 C atoms, and benzoylacetonitrile or derivatives thereof.

Other α-carbonylphenylacetonitrile derivatives are described in numerous publications, thus, for example, in J. Org. Chem., 36, 3160–3168(1971), DE-A 2 033 910, U.S. Pat. No. 3 793 364, Chem. Ber., 91, 1798(1958), CA 87(23): 184219d, 91(5): 39426x, 94(19): 151882f, 97(11): 87060u, 98(17): 138991d, 100(7): 51289s, 103(3): 18295n, 103(25): 215070d, 104(25): 224795s, 106(9): 63041s, 109(11): 92273m, 110(11): 90027f and 110(17): 154213y.

The present invention relates to compositions comprising an organic material liable to thermal, oxidative and/or actinic degradation and at least one compound of the formula I

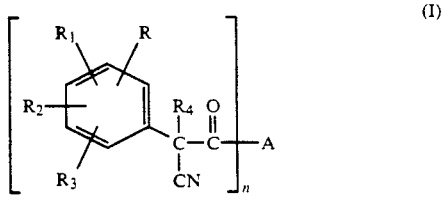

in which

R is hydrogen, —OH, halogen, $C_1$–$C_{20}$alkyl, $C_2$–$C_{20}$alkenyl, $C_5$–$C_{12}$cycloalkyl, $C_1$–$C_4$alkyl-$C_5$–$C_{12}$cycloalkyl, phenyl, naphthyl, $C_1$–$C_{20}$alkoxy, phenyloxy, naphthyloxy, —S—$C_1$–$C_{20}$alkyl, —S-phenyl, —S-naphthyl, —O—CO—$C_1$–$C_{20}$alkyl, —O—CO-phenyl, —O—CO-naphthyl, —COOH, —COO—$C_1$–$C_{20}$alkyl, —COO—$C_2$–$C_{20}$alkenyl, —COO-phenyl, —COO-naphthyl, —CONR'R'', —CO—$C_1$–$C_{20}$alkyl, —CO-phenyl, —CO-naphthyl, —NHCO— $C_1$–$C_{20}$alkyl, —NHCO—$C_2$–$C_{20}$alkenyl, -NHCO-phenyl or -NHCO-naphthyl, $R_1$ can have the same meaning as R, $R_2$ is hydrogen, halogen or $C_1$–$C_4$alkyl and $R_3$ is hydrogen or halogen, or two radicals R, $R_1$, $R_2$ or $R_3$ bonded to one another in the ortho-position together form tetramethylene or —CH=CH—CH=CH—, where the remaining two radicals of R, $R_1$, $R_2$ and $R_3$ are hydrogen, or $R_1$ to $R_3$ are hydrogen and, if $n=1$, R is a group

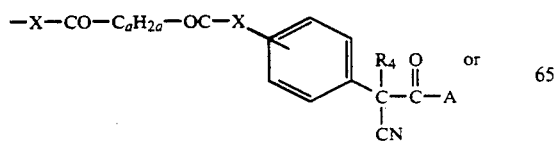

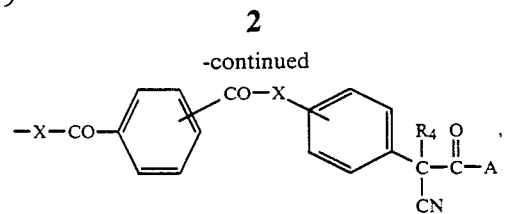

R' and R'' independently of one another are hydrogen, $C_1$–$C_{20}$alkyl, $C_2$–$C_{20}$alkenyl, phenyl or naphthyl or, together with the bonding N atom, form a 5- or 6-membered heterocyclic ring, a is zero to 10, n is 1 to 6, X is —O— or —NH—, $R_4$ is hydrogen or, if $n=1$, is a group

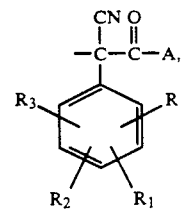

A, if $n=1$ is —OH, —$OR_5$, —$NR_6R_7$, —NH—$NR_8R_9$, $C_1$–$C_{30}$alkyl, $C_2$–$C_{30}$alkenyl, $C_5$–$C_{12}$cycloalkyl, $C_1$–$C_4$alkyl-$C_5$–$C_{12}$cycloalkyl,

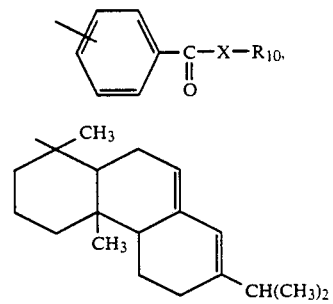

or the corresponding dihydro or tetrahydro derivative, —$C_aH_{2a}$—CO—X—$R_{10}$, —$C_bH_{2b}$—OCO—$R_{10}$, —$C_bH_{2b}$—OH,

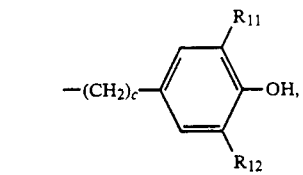

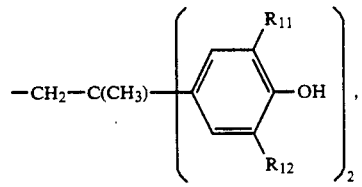

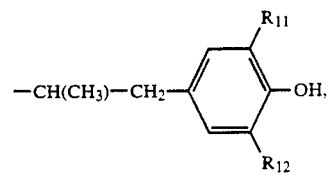

-continued

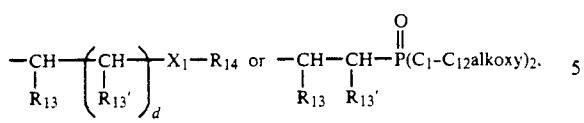

where $R_5$ is $C_1$-$C_{30}$alkyl, $C_2$-$C_{30}$alkenyl, $C_5$-$C_{12}$cycloalkyl, $C_1$-$C_4$alkyl-$C_5$-$C_{12}$cycloalkyl, phenyl-$C_1$-$C_4$alkyl, phenyl, naphthyl, biphenyl, the radical of a terpene alcohol or a radical of the formulae

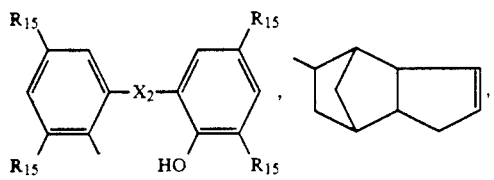

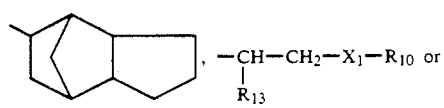

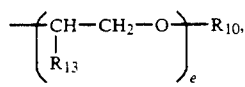

$R_6$ and $R_7$ independently of one another are hydrogen, $C_1$-$C_{20}$alkyl, $C_2$-$C_{20}$alkenyl, $C_5$-$C_{12}$cycloalkyl, $C_1$-$C_4$alkyl-$C_5$-$C_{12}$cycloalkyl, phenyl-$C_1$-$C_4$alkyl, phenyl, naphthyl,

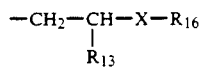

or $-CH_2C(CH_2-O-R_{16})_3$ or $R_6$, if $R_7=H$, can also be $-(CH_2)_f-X-R_{16}$ or $R_6$ and $R_7$, together with the N bonding atom, form a 5- or 6-membered heterocyclic ring, $R_8$ and $R_9$ independently of one another are hydrogen, $C_1$-$C_{20}$alkyl, phenyl, $-CO-C_1$-$C_{20}$-alkyl, $-CO-C_2$-$C_{18}$alkenyl, $-CO$-phenyl or $-CO$-naphthyl or together are $=CH-R_{17}$, $R_{10}$ is hydrogen, $C_1$-$C_{20}$alkyl, $C_2$-$C_{20}$alkenyl, $C_5$-$C_{12}$cycloalkyl, phenyl-$C_1$-$C_4$alkyl, phenyl, naphthyl, $-CO-C_1$-$C_{20}$alkyl, $-CO$-phenyl, $-CO$-naphthyl or

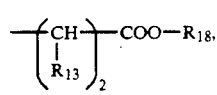

$R_{11}$ and $R_{12}$ independently of one another are hydrogen, $C_1$-$C_4$alkyl, cyclohexyl or phenyl, $R_{13}$ is hydrogen or methyl and $R_{13}'$ is hydrogen, methyl or phenyl, $R_{14}$ is $C_1$-$C_{20}$alkyl, $C_2$-$C_{20}$alkenyl, $C_5$-$C_{12}$cycloalkyl, phenyl-$C_1$-$C_4$alkyl, phenyl or naphthyl, the $R_{15}$ independently of one another are $C_1$-$C_4$alkyl, $R_{16}$ is hydrogen, $-CO-C_1$-$C_{20}$alkyl, $-CO-C_2$-$C_{20}$alkenyl, $-CO$-phenyl or $-CO$-naphthyl, $R_{17}$ is $C_1$-$C_{20}$alkyl, $C_2$-$C_{20}$alkenyl, $C_5$-$C_{12}$cycloalkyl, phenyl, naphthyl, 2-furyl,

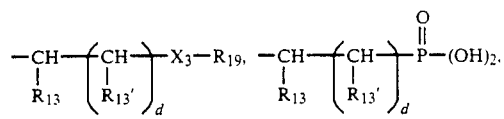

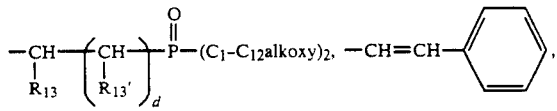

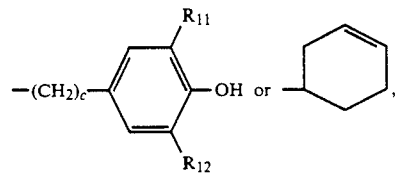

$R_{18}$ is hydrogen, $C_1$-$C_{20}$alkyl or $C_2$-$C_{20}$alkenyl, $R_{19}$ is $C_1$-$C_{20}$alkyl, $C_5$-$C_{12}$cycloalkyl, phenyl or $-CH_2-COO-C_{12}$-$C_{20}$alkyl, X and a are as defined above, $X_1$ is $-O-$, $-S-$, $-NH-$ or $-NR_{14}-$, $X_2$ is a direct bond, $-CH_2-$, $>CH-CH_3$ or $-S-$ and $X_3$ is $-O-$, $-S-$, $-NH-$ or $-NR_{19}-$, b is 3 to 5, c is 0 to 2, d is 0 or 1, e is 2 to 10 and f is 2 to 6;

or A, if $n=2$, is

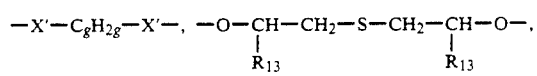

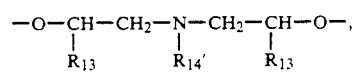

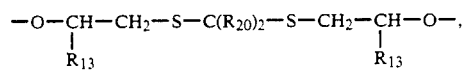

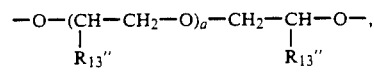

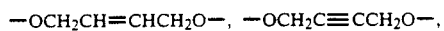

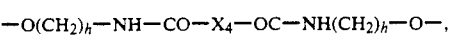

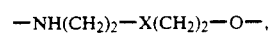

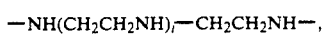

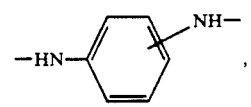

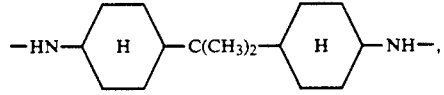

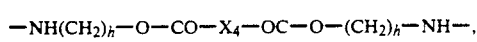

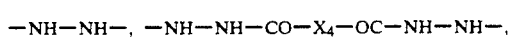

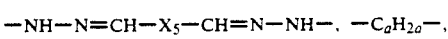

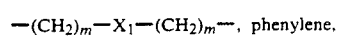

-continued

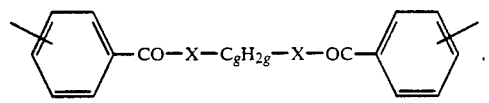

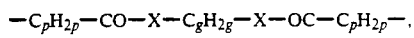

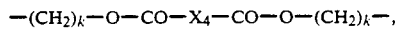

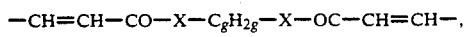

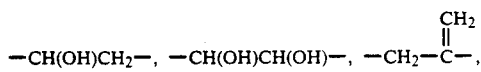

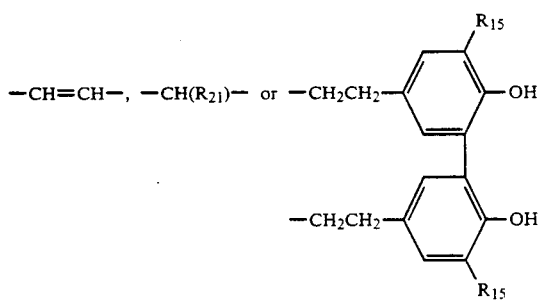

where X, $R_{13}$, $R_{15}$, a and f are as defined above, the X' independently of one another are —O— or —NH—, $R_{13}''$ is hydrogen or methyl and, if a=zero, can also be $C_2$-$C_{18}$alkyl or phenyl, $R_{14}'$ can have the same definition as $R_{14}$ or is hydrogen, the $R_{20}$ independently of one another are hydrogen, $C_1$-$C_{20}$alkyl, phenyl or together are a 5-12-membered cycloaliphatic ring, $R_{21}$ is $C_5$-$C_{12}$cycloalkyl, phenyl-$C_1$-$C_4$alkyl, phenyl or

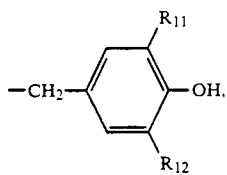

g is 2 to 12, h is 2 to 6, i is 1 to 5, k is 3 to 5, m is 1 or 2 and p is 1 to 10, $X_4$ is —$C_aH_{2a}$—, phenylene or —CH=CH— and $X_5$ is a direct bond, —(CH$_2$)$_3$— or —C(CH$_3$)$_2$—S—S—C(CH$_3$)$_2$—;
or A, if n=3, is

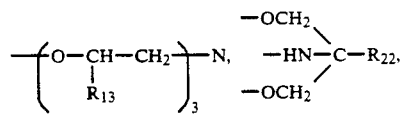

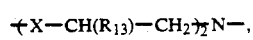

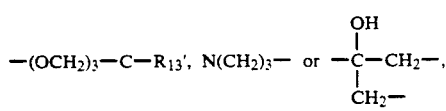

where $R_{13}$ and $R_{13}'$ are as defined above and $R_{22}$ is methyl or ethyl;
or A, if n=4, is C(CH$_2$O)$_4$—,

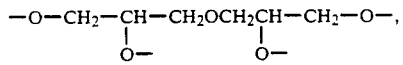

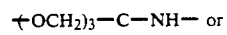

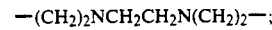

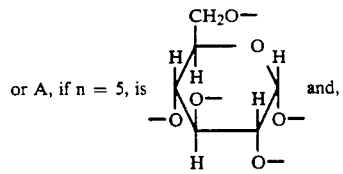

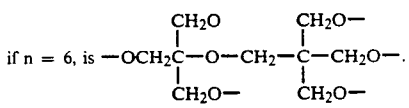

Alkyl, alkoxy or alkenyl groups represented by any radicals or alkyl, alkoxy or alkenyl moieties contained in such radicals can be straight-chain or branched.

Examples of alkyl groups A, R, R', R'', $R_1$, $R_5$ to $R_{10}$, $R_{14}$, $R_{14}'$ and $R_{17}$ to $R_{20}$ having up to 20 or up to 30 C atoms (A or $R_5$) which may be mentioned are: methyl, ethyl, propyl, isopropyl, n-butyl, isobutyl, t-butyl, pentyl, isopentyl, hexyl, heptyl, 3-heptyl, octyl, nonyl, decyl, undecyl, dodecyl, tridecyl, tetradecyl, pentadecyl, hexadecyl, heptadecyl, 2-ethylbutyl, 1-methylpentyl, 1,3-dimethylbutyl, 1,1,3,3-tetramethylbutyl, 1-methylhexyl, 2-ethylhexyl, 1-methylheptyl, 1,1,3-trimethylhexyl, 1-methylundecyl, eicosyl, heneicosyl, docosyl, tricosyl, tetracosyl, pentacosyl, octacosyl and tricontyl.

Alkyl groups R, R', R'', $R_1$ and $R_{20}$ and alkyl moieties in radicals R or $R_1$=—S—$C_1$-$C_{20}$alkyl, —O—CO—$C_1$-$C_{20}$alkyl, —CO—O—$C_1$-$C_{20}$alkyl and —NHCO—$C_1$-$C_{20}$alkyl preferably have 1-12 and in particular 1-4 C atoms. Those particularly preferred are, including the alkyl groups $R_2$, straight-chain alkyl groups having 1-4 C atoms, particularly ethyl and especially methyl.

Alkyl groups A, $R_5$ to $R_{10}$, $R_{14}$, $R_{14}'$, $R_{17}$, $R_{18}$ and $R_{19}$ or alkyl moieties contained in radicals $R_8$, $R_9$ or $R_{16}$ are preferably straight-chain and in particular have 1-18, especially 8-18 C atoms. Alkyl groups $R_{17}$ are in particular straight-chain alkyl groups having 1-11 C atoms.

Examples of alkenyl groups A, R, R', R'', $R_1$, $R_5$ to $R_7$, $R_{10}$, $R_{14}$, $R_{14}'$, $R_{17}$ and $R_{18}$ or of alkenyl moieties contained in such groups or in radicals $R_8$, $R_9$ and $R_{16}$ having 2-18 ($R_8$, $R_9$), 2-20 or 2-30 C atoms (A and $R_5$) which may be mentioned are: vinyl, allyl, methallyl, hexenyl, decenyl, undecenyl, heptadecenyl and oleyl.

Alkenyl groups R, R', R'' and $R_1$ preferably have 3-6 C atoms, while alkenyl groups A, $R_5$ to $R_7$, $R_{10}$, $R_{14}$, $R_{14}'$, $R_{17}$ and $R_{18}$ and alkenyl moieties in radicals $R_8$, $R_9$ and $R_{16}$ advantageously have 2-18 C atoms.

Examples of $C_5$-$C_{12}$cycloalkyl groups A, R, $R_1$, $R_5$, $R_6$, $R_7$, $R_{14}$, $R_{14}'$, $R_{17}$, $R_{19}$ and $R_{21}$ and $C_1$-$C_4$alkyl-$C_5$-$C_{12}$cycloalkyl groups A, R, $R_1$, $R_5$, $R_6$ and $R_7$ are: cyclopentyl, cyclohexyl, methylcyclohexyl, 4-butylcyclohexyl, cycloheptyl, cyclooctyl and cyclododecyl. $C_5$-$C_7$-Cycloalkyl and methyl-$C_5$-$C_7$cycloalkyl, particularly cyclopentyl, methylcyclohexyl and especially cyclohexyl, are preferred.

$R_5$, $R_6$, $R_7$, $R_{10}$, $R_{14}$, $R_{14}'$ and $R_{21}$ as phenyl-$C_1$-$C_4$alkyl are particularly phenylethyl and especially benzyl.

Alkoxy groups R and $R_1$ or alkoxy substituents in groups A can be straight-chain or branched. Examples of these are: methoxy, ethoxy, propoxy, isopropoxy, butoxy, isobutoxy, pentyloxy, hexyloxy, heptyloxy, octyloxy, decyloxy, dodecyloxy, tetradecyloxy, hexadecyloxy and octadecyloxy. Straight-chain alkoxy groups having 1 to 4 C atoms, particularly ethoxy and especially methoxy, are preferred.

If R' and R" or $R_6$ and $R_7$, together with the N bonding atom, form a 5- or 6-membered heterocyclic ring, it is, for example, a pyrrolidine, piperidine, 2,6-dimethylpiperidine, piperazine, 4-methylpiperazine or morpholine ring.

Halogen radicals R, $R_1$, $R_2$ or $R_3$ are, for example, fluorine or bromine atoms, in particular chlorine atoms. $R_2$ and $R_3$ are preferably hydrogen, R and $R_1$, preferably independently of one another, are hydrogen, $C_1$-$C_4$alkyl, $C_1$-$C_4$alkoxy or halogen, particularly chlorine. $R_1$, $R_2$ and $R_3$ are particularly preferably hydrogen and R is hydrogen, $C_1$-$C_4$alkyl, particularly methyl, $C_1$-$C_4$alkoxy, particularly methoxy, or chlorine. R, $R_1$, $R_2$ and $R_3$ are very particularly preferably hydrogen.

If $R_4$ is a group

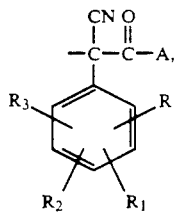

then R, $R_1$, $R_2$ and $R_3$ are as defined above and A is preferably —$OC_1$-$C_{18}$alkyl, particularly —$OC_1$-$C_4$alkyl.

n is preferably 1 or 2.

$R_{11}$ is preferably hydrogen, methyl or tert-butyl and $R_{12}$ is in particular methyl or tert-butyl. One of $R_{11}$ and $R_{12}$ is particularly preferably methyl or tert-butyl and the other tert-butyl.

A as alkyl or alkenyl preferably has 1-17 or 2-17 C. atoms. An A group

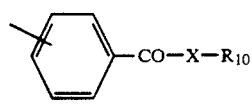

is preferably bonded to the carbonyl group in the m- or p-position. X is in this case in particular —O— and $R_{10}$ is preferably hydrogen, cyclohexyl, methylcyclohexyl, benzyl or $C_2$-$C_{18}$alkenyl and in particular alkyl having 1-18 and especially 1-4 C atoms.

—$C_aH_{2a}$—, —$C_bH_{2b}$—, —$C_gH_{2g}$— and —$C_pH_{2p}$— groups can be straight-chain or branched. These groups are preferably straight-chain or, if n=2 and A=—X'—$C_gH_{2g}$—X'—, are —$CH_2C(CH_3)_2CH_2$—.

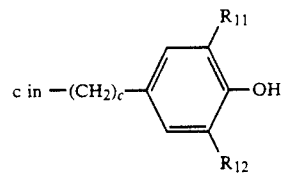

groups is preferably 1 and especially 2.

d is preferably zero. $R_{13}$, $R_{13}'$ and $R_{13}''$ are preferably hydrogen. In —$C_aH_{2a}$—CO—X—$R_{10}$ groups, a is preferably 1-10, X is in particular —O— and $R_{10}$ is hydrogen, $C_1$-$C_{18}$alkyl, $C_2$-$C_{18}$alkenyl, cyclohexyl, methylcyclohexyl or benzyl. In —$C_bH_{2b}$—OCO—$R_{10}$ groups, X is likewise preferably —O—, while $R_{10}$ is preferably $C_1$-$C_{17}$alkyl, $C_2$-$C_{17}$alkenyl or phenyl.

$X_1$ and $X_2$ are preferably —O— and in particular —S—. $X_2$ is in particular a direct bond or >CH—$CH_3$. $X_4$ is preferably —$(CH_2)_a$— where a is preferably 2-8 and in particular 4-8. $X_5$ is preferably —$C(CH_3)_2$—S—S—$C(CH_3)_2$—.

$R_{14}$ is preferably alkyl having 1-18 and in particular 8-18 C atoms.

Possible radicals of terpene alcohols $R_5$ are in particular radicals of acyclic or monocyclic compounds, for example radicals of geraniol, nerol, linalool, citronellol, thymol or menthol.

$R_{10}$ in groups $R_5$=—$CH(R_{13})$—$CH_2$—$X_1$—$R_{10}$ or

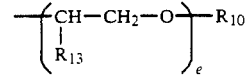

is preferably hydrogen, $C_1$-$C_{18}$alkyl or $C_2$-$C_{18}$alkenyl. e is in this case in particular 2-6 and $X_1$ and $R_{13}$ are as defined above.

$R_5$ is preferably $C_1$-$C_{18}$alkyl, $C_2$-$C_{18}$alkenyl, cyclohexyl, methylcyclohexyl, benzyl, a —$CH(R_{13})$—$CH_2$—$X_1$—$R_{10}''$ group or

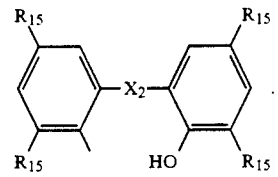

In this case $R_{13}$ is preferably hydrogen, $X_1$ is preferably —O— and in particular —S— and $R_{10}''$ is hydrogen, $C_1$-$C_{18}$alkyl or $C_2$-$C_{18}$alkenyl. $R_5$ is very particularly preferably $C_1$-$C_{18}$alkyl, especially $C_8$-$C_{18}$alkyl, cyclohexyl, methylcyclohexyl, benzyl or a

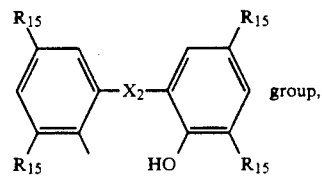 group, in which $X_2$ is a direct bond or >CH—$CH_3$ and the $R_{15}$ independently of one another are methyl or tert-butyl.

Of $R_6$ and $R_7$, one is preferably hydrogen and the other is $C_1$-$C_{18}$alkyl, $C_2$-$C_{18}$alkenyl, cyclohexyl, methylcyclohexyl, benzyl or a group —CH$_2$CH$_2$—X—R$_{16}$ where X=—O— and R$_{16}$=hydrogen, —CO—C$_1$C$_{18}$alkyl or —CO—C$_2$-C$_{18}$alkenyl.

Of R$_8$ and R$_9$, one is preferably hydrogen and the other is hydrogen, C$_1$-C$_{12}$alkyl, —CO—C$_1$-C$_{18}$alkyl or —CO—C$_2$-C$_{18}$alkenyl or R$_8$ and R$_9$ are together =CH—R$_{17}$, in which R$_{17}$ is preferably C$_1$-C$_{11}$alkyl, C$_2$-C$_{11}$alkenyl, —(CH$_2$)$_m$—S—C$_1$-C$_{18}$alkyl or

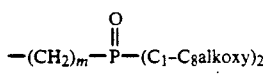

R$_9$ is particularly preferably hydrogen and R$_8$ is hydrogen, —CO—C$_1$-C$_{18}$alkyl, particularly —CO—C$_8$-C$_{18}$alkyl, or —COCH=CH$_2$ or R$_8$ and R$_9$ are together =CH—R$_{17}$ where R$_{17}$=C$_1$-C$_{11}$alkyl,

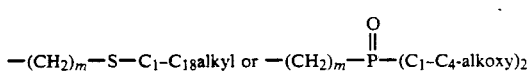

In this case, m is preferably 2.

Preferred definitions of R$_{14}$, R$_{15}$, R$_{16}$ and R$_{17}$ are as above. R$_{18}$ is in particular hydrogen or C$_1$-C$_{18}$alkyl, particularly C$_8$-C$_{18}$alkyl. R$_{19}$ is preferably C$_1$-C$_{18}$alkyl, particularly C$_8$-C$_{18}$alkyl.

The X' preferably have the same definition. —C$_g$H$_{2g}$— is in particular straight-chain alkylene having 2-12 C atoms or —CH$_2$C(CH$_3$)$_2$CH$_2$—.

R$_{14}$' is in particular C$_1$-C$_{18}$alkyl, particularly C$_8$-C$_{18}$alkyl and particularly preferably hydrogen.

The R$_{20}$ preferably have the same definition and are in particular hydrogen or methyl. h is preferably 2 and X$_4$ is preferably —(CH$_2$)$_a$—, in which a is in particular 2-8 and particularly preferably 4-8. X$_5$ is preferably —C(CH$_3$)$_2$—S—S—C(CH$_3$)$_2$—. k and f are preferably 5. R$_{21}$ is preferably benzyl, phenyl or

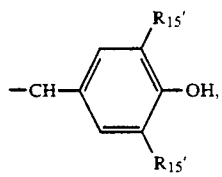

in which the R$_{15}$' independently of one another are methyl or tert-butyl.

Preferred compositions according to the invention are those in which R and R$_1$ independently of one another are hydrogen, C$_1$-C$_4$alkyl, C$_1$-C$_4$alkoxy or halogen, particularly chlorine, and R$_2$ and R$_3$ are hydrogen. According to a further preferred embodiment, compositions are used in which R is hydrogen, C$_1$-C$_4$alkyl, particularly methyl, C$_1$-C$_4$alkoxy, particularly methoxy, or chlorine and R$_1$, R$_2$ and R$_3$ are hydrogen.

Of particular interest are compositions according to the invention comprising compounds of the formula I in which R is hydrogen, C$_1$-C$_4$alkyl, C$_1$-C$_4$alkoxy or chlorine, R$_1$, R$_2$, R$_3$ and R$_4$ are hydrogen, n is 1 or 2, A, if n=1, is —OR$_5$, —NHR$_6$, —NH—NH—R$_8$, —NH—N=CH—R$_{17}$, C$_1$-C$_{17}$alkyl, C$_2$-C$_{17}$alkenyl, -continued

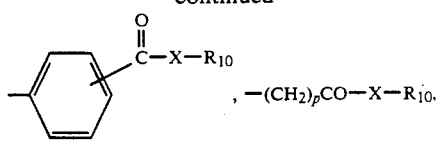

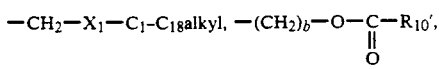

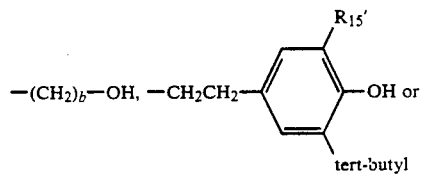

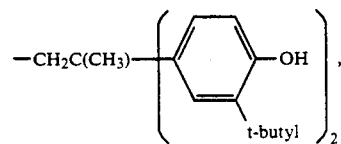

R$_{10}$ is hydrogen, C$_1$-C$_{18}$alkyl, C$_2$-C$_{18}$alkenyl, cyclohexyl, methylcyclohexyl or benzyl and R$_{10}$' is C$_1$-C$_{17}$alkyl, C$_2$-C$_{17}$alkenyl or phenyl, R$_5$ is C$_1$-C$_{18}$alkyl, C$_2$-C$_{18}$alkenyl, cyclohexyl, methylcyclohexyl, benzyl,

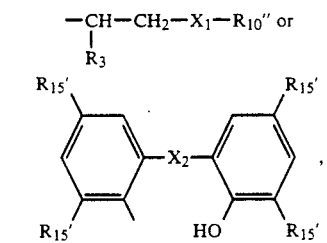

in which R$_{10}$" is hydrogen, C$_1$-C$_{18}$alkyl or C$_2$-C$_{18}$alkenyl and the R$_{15}$' independently of one another are methyl or tert-butyl, R$_6$ is C$_1$-C$_{18}$alkyl, C$_2$-C$_{18}$alkenyl, cyclohexyl, methylcyclohexyl, benzyl, —CH$_2$CH$_2$OH,

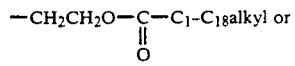

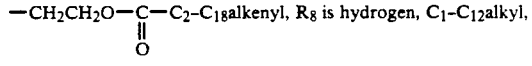

—CO—C$_1$-C$_{18}$alkyl or —CO—C$_2$-C$_{18}$alkenyl, R$_{17}$ is C$_1$-C$_{11}$alkyl, C$_2$-C$_{11}$alkenyl, —(CH$_2$)$_m$—S—C$_1$-C$_{18}$alkyl or

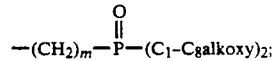

or A, if n = 2, is —O—(CH$_2$)$_g$—O—, —NH—(CH$_2$)$_g$—NH—,

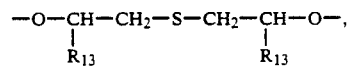

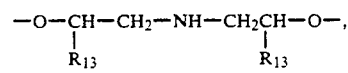

-continued $-O-(CH-CH_2O)_{a'}-CH_2CH-O-$ where a' is zero to 5 or
  |                       |
  $R_{13}$                $R_{13}$ $-OCH_2-C(CH_3)_2CH_2-O-$,
$-NHCH_2CH_2-X-CH_2CH_2O-$,
$-NH(CH_2CH_2NH)_i-CH_2CH_2NH-$,
$-NH-C(CH_3)_2-CH_2O-$, $-NHCH_2CH_2O\overset{O}{\overset{\|}{C}}(CH_2)_a\overset{O}{\overset{\|}{C}}OCH_2CH_2NH-$, $-NH-NH-\overset{O}{\overset{\|}{C}}(CH_2)_a\overset{O}{\overset{\|}{C}}-NH-NH-$, $-NH-N=CH-X_5-CH=N-NH-$, $-(CH_2)_p-$, phenylene,

[structure: two para-substituted benzoyl groups connected by $-C(=O)-X-(CH_2)_g-X-C(=O)-$]

$-(CH_2)_p-\overset{O}{\overset{\|}{C}}-X-(CH_2)_g-X-\overset{O}{\overset{\|}{C}}-(CH_2)_p-$, $-(CH_2)_5-O-\overset{O}{\overset{\|}{C}}-(CH_2)_a-\overset{O}{\overset{\|}{C}}-O-(CH_2)_5-$, $-CH(R_{21})-$ where $R_{21}$ is benzyl, phenyl or

[structure: $-CH_2-$ attached to phenol with two $R_{15'}$ substituents ortho to OH]  —OH or A is

[structure: biphenyl with two $-CH_2CH_2-$ linker groups, two OH groups and two $R_{15'}$ substituents]

and a, b, g, i, m, p, X, $X_1$, $X_2$, $X_5$ and $R_{13}$ are as defined above.

Advantageous compositions according to the invention contain compounds of the formula I in which R is hydrogen, chlorine, methyl or methoxy and $R_1$, $R_2$, $R_3$ and $R_4$ are hydrogen, n is 1 or 2, A, if n=1, is $-OR_5$, $-NHR_6$, $-NH-NH-R_8$, $-NH-N=CH-R_{17}$, $C_1-C_{17}$alkyl, $-(CH_2)_p-COOH$, $-(CH_2)_p-\overset{O}{\overset{\|}{C}}-O-C_1-C_{18}$alkyl, $-(CH_2)_bOH$, $-(CH_2)_b-OCO-C_1-C_{18}$alkyl, $-CH_2-S-C_1-C_{18}$alkyl, [phenyl]$-COO-C_1-C_{18}$alkyl or -continued $-CH_2CH_2-$[phenyl with $R_{15'}$ and tert-butyl]$-OH$  where $R_5$ is $C_1-C_{18}$alkyl, cyclohexyl, methylcyclohexyl, benzyl or

[structure: biphenyl with four $R_{15'}$ groups, $X_2$ bridge, and OH], $R_6$ is $C_1-C_{18}$alkyl, cyclohexyl, benzyl, $-(CH_2)_f-OH$ or $-CH_2CH_2O-CO-C_1-C_{18}$alkyl, $R_8$ is hydrogen, $-CO-C_1-C_{18}$alkyl or $-COCH=CH_2$,
the $R_{15'}$ independently of one another are methyl or tert-butyl,
$R_{17}$ is $C_1-C_{11}$alkyl, $-(CH_2)_m-S-C_1-C_{18}$alkyl or $-(CH_2)_m-\overset{O}{\overset{\|}{P}}-(C_1-C_4\text{alkoxy})_2$, or A, if n = 2, is $-O-(CH_2)_g-O-$, $-NH-(CH_2)_f-NH-$,
$-OCH_2CH_2SCH_2CH_2O-$, $-O(CH_2CH_2O)_c-CH_2CH_2-O-$,
$-OCH_2C(CH_3)_2CH_2O-$, $-NHCH_2CH_2OCH_2CH_2O-$, $-NHCH_2CH_2O\overset{O}{\overset{\|}{C}}(CH_2)_a\overset{O}{\overset{\|}{C}}OCH_2CH_2NH-$, $-NH-NH-\overset{O}{\overset{\|}{C}}(CH_2)_a\overset{O}{\overset{\|}{C}}-NH-NH-$, $-NH-N=CH-C(CH_3)_2-S-S-C(CH_3)_2-CH=N-NH-$, phenylene or $-(CH_2)_p-$, where a, b, c, f, g, m, p and $X_2$ are as defined above.

Particularly preferred compositions are those in which R is chlorine, methyl or methoxy and in particular hydrogen, $R_1$, $R_2$, $R_3$ and $R_4$ are hydrogen, n is 1 or 2, A, if n=1, is $-OR_5$, $-NHR_6$, $-NH-NH-R_8$, $-NH-N=CH-R_{17}$, $C_8-C_{17}$alkyl, $-(CH_2)_{p'}-CO-O-C_8-C_{18}$alkyl where p'=2 to 6, $-(CH_2)_b-OH$, $-(CH_2)_b-OCO-C_8-C_{18}$alkyl, $-CH_2-S-C_8-C_{18}$alkyl,

[phenyl]$-COO-C_1-C_4$alkyl or $-CH_2CH_2-$[phenyl with two $R_{15'}$]$-OH$, $R_5$ is [biphenyl with four $R_{15'}$, $X_2$, and HO] and in particular $C_8-C_{18}$alkyl, $R_6$ is $C_8-C_{18}$alkyl, $-(CH_2)_{f'}-OH$ where f' = 2 or 3 or $-CH_2CH_2OCO-C_8-C_{18}$alkyl, -continued $R_8$ is $-CO-C_8-C_{18}$alkyl or $-COCH=CH_2$.
$R_{17}$ is $C_8-C_{11}$alkyl, $(CH_2)_m-S-C_8-C_{18}$alkyhl or $$-(CH_2)_m-\overset{O}{\underset{\|}{P}}-(C_1-C_4alkoxy)_2.$$

or A, if n=2, is $-O(CH_2)_gO-$, $-NH(CH_2)_gNH-$, $-OCH_2CH_2SCH_2CH_2O-$, $-O(CH_2CH_2O)_cCH_2CH_2O-$, $-OCH_2C(CH_3)_2CH_2O-$, $-NHCH_2CH_2OCH_2CH_2O-$, $-NHCH_2CH_2OCO-(CH_2)_{a'}-OCOCH_2CH_2NH-$ or $-NH-NHCO-(CH_2)_{a'}-CONH-NH-$ where $a''=2$ to 8, is $-NH-N=CH-C(CH_3)_2-S-S-C(CH_3)_2-CH=N-NH-$, $-(CH_2)_{p''}-$ where $p''=5-10$ or phenylene, b is 3 to 5, particularly 5, $X_2$ is a direct bond or $>CH-CH_3$ and $R_{15}'$, c, g, and m are as defined above. Very particularly preferred compositions are those in which R, $R_1$, $R_2$, $R_3$ and $R_4$ are hydrogen, n is 1 or 2, A, if n=1, is $C_8-C_{17}$alkyl, $-OR_5$, $-NHR_6$ or $-NH-NH-CO-C_8-C_{17}$alkyl, $R_5$ and $R_6$ independently of one another are $C_8-C_{18}$alkyl, or A, if n=2, is $-O(CH_2)_g-O-$, $-NH(CH_2)_gNH-$, $-OCH_2C(CH_3)_2CH_2O-$, $-NH-NHCO-CH_2CH_2-OCNH-NH-$, $-(CH_2)_{p''}-$ where $p''=5$ to 10 or phenylene, where g is as defined above.

Also preferred are compositions comprising a compound of the formula Ia

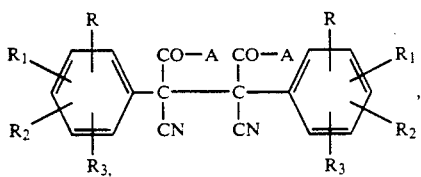

in which R is hydrogen, $C_1-C_4$alkyl, $C_1-C_4$alkoxy or chlorine, $R_1$, $R_2$ and $R_3$ are hydrogen and A is $-OC_1-C_{18}$alkyl, particularly $-OC_1-C_4$alkyl, in particular those containing compounds of the formula Ia in which R, $R_1$, $R_2$ and $R_3$ are hydrogen and A is $-OC_1-C_4$alkyl.

The materials contained in the compositions according to the invention are those which are sensitive to oxidative, thermal and/or actinic degradation. Living organisms are to be understood as not coming under these organic materials.

Examples of organic materials which may be mentioned which can be stabilised according to the invention with the aid of the compounds of the formula I are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene; as well as polyethylene (which if desired can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low-density polyethylene (LLDPE) and its mixtures with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and their salts (ionomers) and terpolymers of ethylene with propylene and a diene, such as hexadiene, dicyclopentadiene or ethylidenenorbornene; as well as mixtures of such copolymers with each other and with polymers mentioned under 1), for example polypropylene/ethylene-propylene copolymers, LDPE/ethylene-vinylacetate copolymers, LDPE/ethylene-acrylic acid copolymers, LLDPE/ethylene-vinylacetate copolymers and LLDPE/ethylene acrylic acid copolymers.

3a. Hydrocarbon resins (for example $C_5-C_9$) including hydrogenated modifications thereof (for example tackifier resins).

4. Polystyrene, poly-(p-methylstyrene), poly-(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic anhydride, styrene/acrylonitrile/methyl acrylate; mixtures of high impact strength from copolymers of styrene and another polymer, for example from a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene or α-methylstyrene, for example styrene on polybutadiene; styrene on copolymers of polybutadiene-styrene or polybutadiene-acrylonitrile; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene; styrene and acrylonitrile on ethylene/propylene/diene terpolymers; styrene and acrylonitrile on polyalkylacrylates or polyalkylmethacrylates; styrene and acrylonitrile on acrylate/butadiene copolymers, as well as mixtures thereof with the copolymers mentioned under 5), for example those known as so-called ABS, MBS, ASA and AES polymers.

7. Halogen-containing polymers, such as polychloroprene, chlorinated rubber, chlorinated or sulfochlorinated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride, as well as copolymers thereof, such as vinyl chloride/vinylidene chloride, vinyl chloride/vinyl acetate or vinylidene chloride/vinyl acetate.

8. Polymers which are derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in item 1).

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain comonomers, ethylene oxide for example; polyacetals modified with thermoplastic polyurethanes, acrylates or MBS.

13. Polyphenylene oxides and sulfides, and mixtures thereof with styrene polymers or polyamides.

14. Polyurethanes which are derived from polyethers, polyesters and polybutadienes with terminal hydroxyl groups on the one hand and aliphatic or aromatic polyisocyanates on the other hand, as well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained starting from m-xylenediamine and adipic acid; polyamides prepared from hexamethylenediamine and isophthalic and/or terephthalic acid and if desired an elastomer as modifier, for example poly-2,4,4-trimethyl-hexamethylene terephthalamide or poly-m-phenylene-isophthalamide. Block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. In addition, polyamides or copolyamides modified with EPDM or ABS; as well as polyamides condensed during processing (RIM-polyamide systems).

16. Polyureas, polyimides, polyamide-imides and polybenzimidazoles.

17. Polyesters which are derived from dicarboxylic acids and dialcohols and/or from hydroxy-carboxylic acids or the corresponding lactones, such as polyethylene terephtalate, polybutylene terephthalate, poly-1,4-dimethylolcyclohexane terephthalate, polyhydroxybenzoate, as well as block polyether-esters derived from polyethers having hydroxyl end groups; in addition polyesters modified with polycarbonates or MBS.

18. Polycarbonates and polyester-carbonates.

19. Polysulfones, polyether-sulfones and polyetherketones.

20. Crosslinked polymers which are derived from aldehydes on the one hand and phenols, urea or melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins, derived from substituted acrylic esters, for example epoxy-acrylates, urethane-acrylates or polyester-acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bis-glycidyl ethers or from cycloaliphatic diepoxides.

26. Natural polymers, such as cellulose, natural rubber, gelatin and derivatives thereof which are chemically modified in a polymer-homologous manner, such as cellulose acetates, cellulose propionates and cellulose butyrates, or cellulose ethers, such as methylcellulose; and rosins and their derivatives.

27. Mixtures (polyblends) of the polymers mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6/6 and copolymers, PA/HDPE, PA/PP, PA/PPO.

28. Naturally occurring and synthetic organic materials which are pure monomeric compounds or mixtures of such compounds, for example mineral oils, animal or vegetable fats, oil and waxes, or oils, waxes and fats based on synthetic esters (e.g. phthalates, adipates, phosphates or trimellitates) and also mixtures of synthetic esters with mineral oils in any weight ratio, which mixtures may be used for example as spinning preparations, as well as aqueous emulsions thereof.

29. Aqueous emulsions of natural or synthetic rubbers, for example natural latex or latices of carboxylated styrene/butadiene copolymers.

As the organic material, the compositions according to the invention preferably contain a lubricant, a metal processing fluid, a hydraulic fluid or a natural, semi-synthetic or synthetic polymer. Halogen-free polymers are preferred. Compositions are particularly preferred which contain a halogen-free thermoplastic or an elastomer. According to a further preferred embodiment, the organic material is a polyolefin. Examples of such polymers are to be taken from the above list of suitable materials.

Compositions are also preferred which contain a lubricant, a metal processing fluid or a hydraulic fluid, in particular a lubricant, as the organic material.

The lubricants in question are based, for example, on mineral or synthetic oils or mixtures thereof. The lubricants are familiar to the person skilled in the art and are described in the relevant specialist literature, for example in Dieter Klamann, "Schmierstoffe und verwandte Produkte" [Lubricants and Related Products] (Verlag Chemie, Weinheim, 1982), in Schewe-Kobek, "Das Schmiermittel-Taschenbuch" [The Lubricant Handbook] (Dr. Alfred Hüthig-Verlag, Heidelberg, 1974) and in "Ullmanns Enzyklopädie der technischen Chemie" [Ullmann's Encyclopaedia of Industrial Chemistry], vol. 13, pages 85-94 (Verlag Chemie, Weinheim, 1977).

The lubricants are in particular oils and fats, for example based on a mineral oil. Oils are preferred.

A further group of lubricants which can be used are vegetable or animal oils, fats, tallows and waxes or mixtures thereof with each other or mixtures with the mineral or synthetic oils mentioned. Vegetable and animal oils, fats, tallows and waxes are, for example, palm kernel oil, palm oil, olive oil, rapeseed oil, rape oil, linseed oil, groundnut oil, soya bean oil, cotton oil, sunflower oil, pumpkin seed oil, coconut oil, maize oil, castor oil, walnut oil and mixtures thereof, fish oils, tallows from slaughtered animals such as bovine tallow, neat's foot oil and bone oil and their modified, epoxidised and sulfoxidised forms, for example epoxidised soya bean oil.

The mineral oils are based in particular on hydrocarbon compounds.

Examples of synthetic lubricants include lubricants based on aliphatic or aromatic carboxylic esters, the polymeric esters, the polyalkylene oxides, the phosphoric acid esters, the poly-α-olefins or the silicones, on a diester of a dibasic acid with a monohydric alcohol, for example dioctyl sebacate or dinonyl adipate, on a triester of trimethylolpropane with a monobasic acid or with a mixture of such acids, for example trimethylolpropane tripelargonate, trimethylolpropane tricaprylate or mixtures thereof, on a tetraester of pentaerythritol with a monobasic acid or with a mixture of such acids, for example pentaerythritol tetracaprylate, or on a complex ester of monobasic and dibasic acids with polyhydric alcohols, for example a complex ester of trimethylolpropane with caprylic and sebacic acid or of a mixture thereof. Particularly suitable in addition to mineral oils are, for example, poly-α-olefins, lubricants based on esters, phosphates, glycols, polyglycols and polyalkylene glycols, and mixtures thereof with water.

Metal processing fluids and hydraulic fluids can be prepared based on the same substances as described above for the lubricants. Frequently, these are also emulsions of such substances in water or other fluids.

The compounds of the formula I are in general added to the organic material in amounts of 0.01 to 10% by weight, for example in amounts of 0.05 to 5, preferably 0.05 to 3% by weight and in particular in amounts of 0.1 to 2% by weight, based on the organic material. Mixtures of various compounds of the formula I can also be employed.

Incorporation into the organic materials can be carried out, for example, by mixing in the compounds of the formula I and, if desired, other additives by the methods customary in industry. If they are polymers, in particular synthetic polymer, incorporation can be carried out before or during moulding, or by applying the dissolved or dispersed compounds to the polymer, if appropriate with subsequent evaporation of the solvent. In the case of elastomers, these can also be stabilised as latices. A further possibility for incorporation of the compounds of the formula I in polymers comprises their addition before, during or immediately after polymerisation of the corresponding monomers or before crosslinking. The compounds of the formula I can be added here as such, but also in encapsulated form (for example in waxes, oils or polymers). In the case of addition before or during polymerisation, the compounds of the formula I can also act as regulators for the chain length of the polymers (chain terminators).

The compounds of the formula I or mixtures thereof can also be added to the plastics to be stablised in the form of a masterbatch which contains these compounds, for example, in a concentration of 2.5 to 25% by weight.

The incorporation of the compounds of the formula I can advantageously be carried out by the following methods:
- as an emulsion or dispersion (for example to give latices or emulsion polymers)
- as a dry mixture during mixing of additive components or polymer mixtures
- by direct addition to the processing apparatus (for example extruders, internal mixers etc.)
- as a solution or melt.

Polymer compositions according to the invention can be used in various forms or processed to give various products, for example as (to give) foils, fibres, tapes, moulded materials, profiles or as binders for paints, adhesives or cement.

Lubricant compositions according to the invention are used, for example, in internal combustion engines, for example in motor vehicles.

In addition to the compounds of the formula I or mixtures thereof, the compositions according to the invention can also contain other stabilisers, particularly antioxidants, light stabilisers and processing stabilisers (heat stabilisers), in particular if they contain organic, preferably synthetic polymers. Examples of such additives are:

1. Antioxidants 1.1. Alkylated monophenols, for example
2,6-di-tert-butyl-4-methylphenol,
2-tert-butyl-4,6-dimethylphenol, 2,6-di-tert-butyl-4-ethylphenol,
2,6-di-tert-butyl-4-n-butylphenol, 2,6-di-tert-butyl-4-isobutylphenol,
2,6-dicyclopentyl-4-methylphenol, 2-(α-methylcyclohexyl)-4,6-dimethylphenol,
2,6-dioctadecyl-4-methylphenol, 2,4,6-tricyclohexylphenol,
2,6-di-tert-butyl-4-methoxymethylphenol, 2,6-dinonyl-4-methylphenol.

1.2. Alkylated hydroquinones, for example
2,6-di-tert-butyl-4-methoxyphenol,
2,5-di-tert-butylhydroquinone, 2,5-di-tert-amylhydroquinone,
2,6-diphenyl-4-octadecyloxyphenol.

1.3. Hydroxylated diphenylthio ethers, for example
2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example
2,2'-methylenebis(6-tert-butyl-4-methylphenol),
2,2'-methylenebis(6-tert-butyl-4-ethylphenol),
2,2'-methylenebis[4-methyl-6-(α-methylcyclohexyl)phenol],
2,2'-methylenebis(4-methyl-6-cyclohexylphenol),
2,2'-methylenebis(6-nonyl-4-methylphenol), 2,2'-methylenebis(4,6-di-tert-butylphenol),
2,2'-ethylidenebis(4,6-di-tert-butylphenol),
2,2'-ethylidenebis(6-tert-butyl-4-isobutylphenol),
2,2'-methylenebis[6-(α-methylbenzyl)-4-nonylphenol],
2,2'-methylenebis[6-(α,α-dimethylbenzyl)-4-nonylphenol],
4,4'-methylenebis(2,6-di-tert-butylphenol),
4,4'-methylenebis(6-tert-butyl-2-methylphenol),
1,1-bis(5-tert-butyl-4-hydroxy-2-methylphenyl)butane,
2,6-bis(3-tert-butyl-5-methyl-2-hydroxybenzyl)-4-methylphenol,
1,1,3-tris(5-tert-butyl-4-hydroxy-2-methylphenyl)butane, 1,1-bis(5-tert-butyl-4-hydroxy-2-methylphenyl)-3-n-dodecylmercaptobutane,
ethylene glycol bis[3,3-bis(3'-tert-butyl-4'-hydroxyphenyl)butyrate],
bis(3-tert-butyl-4-hydroxy-5-methylphenyl)dicyclopentadiene,
bis[2-(3'-tert-butyl-2'-hydroxy-5'-methylbenzyl)-6-tert-butyl-4-methylphenyl]terephthalate.

1.5. Benzyl compounds, for example
1,3,5-tris(3,5-di-tert-butyl-4-hydroxybenzyl)-2,4,6-trimethylbenzene,
bis(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate,
1,3,5-tris(4-tert-butyl-3-hydroxy-2,6-dimethylbenzyl) isocyanurate,
dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl) carbamate.

1.7. Esters of β-(3,5-di-tert-butyl-4-hydroxyphenyl)-propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'bis(hydroxyethyl)oxalic acid diamide.

1.9. Esters of β-(3,5-dicyclohexyl-4-hydroxyphenyl)-propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide.

1.10. Amides of β-(3,5-di-tert-butyl-4-hydroxyphenyl)propionic acid for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and Light Stabilisers 2.1. 2-(2'-Hydroxyphenyl)benzotriazoles, for example the
5'-methyl, 3',5'-di-tert-butyl,
5'-tert-butyl,5'-(1,1,3,3-tetramethylbutyl), 5-chloro-3',5'-di-tert-butyl,
5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of unsubstituted or substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenylundecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone).

2.7. Oxalic acid diamides, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted oxanilides, and o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine,
2-(2,4-dihydroxyphenyl)-4,6-bis(2,4-dimethylphenyl)-1,3,5-triazine,
2,4-bis(2-hydroxy-4-propyloxyphenyl)-6-(2,4-dimethylphenyl)-1,3,5-triazine,
2-(2-hydroxy-4-octyloxyphenyl)-4,6-bis(4-methylphenyl)-1,3,5-triazine,
2-(2-hydroxy-4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl)

phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite.

5. Compounds which destroy peroxides, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticisers, lubricants, emulsifiers, pigments, fluorescent whitening agents, flameproofing agents, antistatic agents and blowing agents.

If the compositions according to the invention are those based on lubricants and hydraulic fluids or metal processing fluids, they can also contain other additives which are added to improve certain use properties, for example other antioxidants, metal deactivators, rust inhibitors, viscosity index improvers, pour point reducers, dispersants/surfactants and abrasion resistance additives.

Examples of antioxidants are to be taken from the listing reproduced further above under the title "1. Antioxidants", in particular items 1.1 to 1.10. Examples of other additional additives are the following:

EXAMPLES OF AMINE ANTIOXIDANTS:

N,N'-di-isopropyl-p-phenylenediamine, N,N'-di-sec-butyl-p-phenylenediamine,
N,N'-bis(1,4-dimethyl-pentyl)-p-phenylenediamine,
N,N'-bis(1-ethyl-3-methyl-pentyl)-p-phenylenediamine,
N,N'-bis(1-methyl-heptyl)-p-phenylenediamine, N,N'-dicyclohexyl-p-phenylenediamine,
N,N'-diphenyl-p-phenylenediamine, N,N'di-(naphthyl-2)-p-phenylenediamine,
N-isopropyl-N'-phenyl-p-phenylenediamine,
N-(1,3-dimethyl-butyl)-N'-phenyl-p-phenylenediamine,
N-(1-methyl-heptyl)-N'-phenyl-p-phenylenediamine,
N-cyclohexyl-N'-phenyl-p-phenylenediamine, 4-(p-toluene-sulfonamido)-diphenylamine,
N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylamino-phenol, 4-nonanoylaminophenol, 4-dodecanoylaminophenol, 4-octadecanoylaminophenol, di-(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diamino-diphenylmethane, 1,2-di-[(2-methylphenyl)amino]ethane, 1,2-di-(phenylamino)-propane, (o-tolyl)-biguanide, di-[4-(1',3'-dimethyl-butyl)-phenyl]amine, tert-octylated N-phenyl-1-naphthylamine, mixture of mono- and dialkylated tert-butyl/tert-octyldiphenylamines, 2,3-dihydro-3,3-dimethyl-4H-1,4-benzothiazine, phenothiazine, N-allylphenothiazine.

Examples of other antioxidants: aliphatic or aromatic phosphites, esters of thiodipropionic acid or thiodiacetic acid, or salts of dithiocarbamic or dithiophosphoric acid.

Examples of metal deactivators, for example for copper, are: triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylenebisbenzotriazole, 4,5,6,7-tetrahydrobenzotriazole, salicylidenepropylenediamine, salicylaminoguanidine and salts thereof.

Examples of rust inhibitors are:

a) Organic acids, their esters, metal salts and anhydrides, for example: N-oleoylsarcosine, sorbitan monooleate, lead naphthenate, alkenylsuccinic anhydride, for example dodecenylsuccinic anhydride, alkenylsuccinic acid partial esters and partial amides, 4-nonylphenoxyacetic acid.

b) Nitrogen-containing compounds, for example: I. Primary, secondary or tertiary aliphatic or cycloaliphatic amines and amine salts of organic and inorganic acids, for examples oil-soluble alkylammonium carboxylates.

II. Heterocyclic compounds, for example: substituted imidazolines and oxazolines.

c) Phosphorus-containing compounds, for example: amine salts of phosphoric acid partial esters or phosphonic acid partial esters, zinc dialkyldithiophosphates.

d) Sulfur-containing compounds, for example: barium dinonylnaphthalenesulfonates, calcium petroleumsulfonates.

Examples of viscosity index improvers are: polyacrylates, polymethacrylates, vinylpyrrolidone/methacrylate copolymers, polyvinylpyrrolidones, polybutenes, olefin copolymers, styrene/acrylate copolymers, polyethers.

Examples of pour point reducers are: polymethacrylate, alkylated naphthalene derivatives.

Examples of dispersants/surfactants are: polybutenylsuccinamides or -imides, polybutenylphosphonic acid derivatives, basic magnesium, calcium, and barium sulfonates and phenolates.

Examples of abrasion resistance additives are: sulfur- and/or phosphorus- and/or halogen-containing compounds, such as sulfurised vegetable oils, zinc dialkyldithiophosphates, tritolyl phosphate, chlorinated paraffins, alkyl and aryl di- and tri-sulfides, triphenyl phosphorothionates, diethanolaminomethyltolyltriazole, di(2-ethylhexyl)aminomethyltolyltriazole.

The compounds of the formula I are in particular suitable as processing stabilisers (heat stabilisers) for synthetic polymers which are preferably halogen-free or lubricants which are preferably halogen-free. They are additionally often distinguished by a colour-improving effect in the said polymers.

The invention further relates to novel compounds of the formula Ib

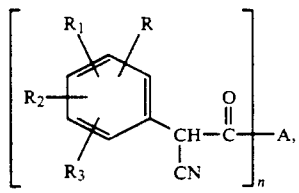
(Ib)

in which R is hydrogen, —OH, halogen, $C_1$-$C_{20}$alkyl, $C_2$-$C_{20}$alkenyl, $C_5$-$C_{12}$cycloalkyl, $C_1$-$C_4$alkyl—$C_5$-$C_{12}$cycloalkyl, phenyl, naphthyl, $C_1$-$C_{20}$alkoxy, phenyloxy, naphthyloxy, —S—$C_1$-$C_{20}$alkyl, —S—phenyl, —S—naphthyl, —O—CO—$C_1$-$C_{20}$alkyl, —O—CO-phenyl, —O—CO-naphthyl, —COOH, —COO—$C_1$-$C_{20}$alkyl, —COO—$C_2$-$C_{20}$alkenyl, —COO-phenyl, —COO-naphthyl, —CONR'R'', —CO—$C_1$-$C_{20}$alkyl, —CO-phenyl, —CO-naphthyl, —NHCO—$C_1$-$C_{20}$alkyl, —NHCO—$C_2$-$C_{20}$alkenyl, —NHCO-phenyl or —NHCO-naphthyl, $R_1$ can have the same definition as R, $R_2$ is hydrogen, halogen or $C_1$-$C_4$alkyl and $R_3$ is hydrogen or halogen, or two radicals R, $R_1$, $R_2$ or $R_3$ bonded to one another in the ortho-position together form tetramethylene or —CH=CH—CH=CH—, where the remaining two of R, $R_1$, $R_2$ and $R_3$ are hydrogen, or $R_1$ to $R_3$ are hydrogen and R, if n=1, is a group

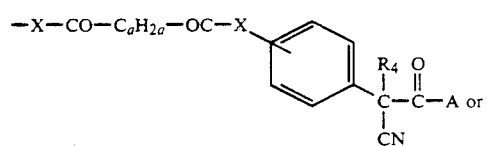

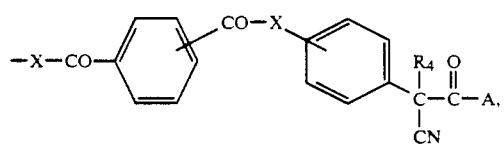

R' and R'' independently of one another are hydrogen, $C_1$-$C_{20}$alkyl, $C_2$-$C_{20}$alkenyl, phenyl or naphthyl or, together with the bonding N atom, form a 5- or 6-membered heterocyclic ring, a is zero to 10, n is 1 to 6, X is —O— or —NH—, A, if n=1, is —OR$_5$, —NR$_6$R$_7$, —NH—NR$_8$R$_9$, $C_1$-$C_{30}$alkyl, $C_2$-$C_{30}$alkenyl, $C_5$-$C_{12}$cycloalkyl, $C_1$-$C_4$alkyl—$C_5$-$C_{12}$cycloalkyl,

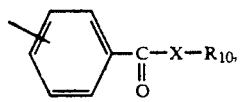

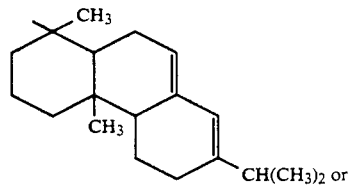

the corresponding dihydro or tetrahydro derivative,

—$C_aH_{2a}$—CO—X—$R_{10}$, —$C_bH_{2b}$—OCO—$R_{10}$, —$C_bH_{2b}$—OH,

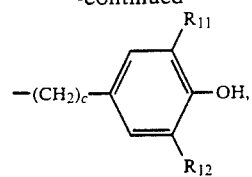

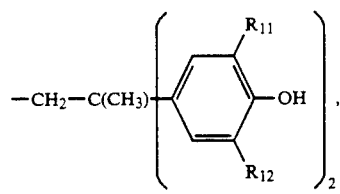

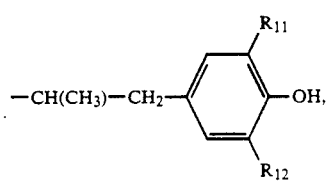

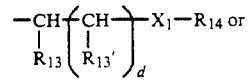

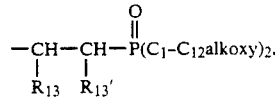

where
$R_5$ is $C_1$-$C_{30}$alkyl, $C_2$-$C_{30}$alkenyl, —$C_5$-$C_{12}$cycloalkyl, $C_1$-$C_4$alkyl—$C_5$-$C_{12}$cycloalkyl, phenyl-$C_1$-$C_4$alkyl, phenyl, naphthyl, biphenyl, the radical of a terpene alcohol or a radical of the formula

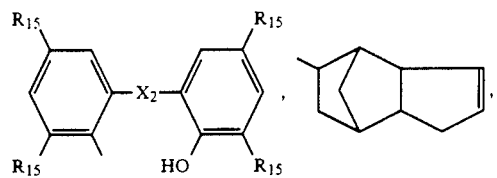

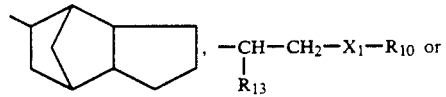

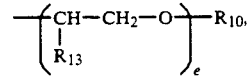

$R_6$ and $R_7$ independently of one another are hydrogen, $C_1$-$C_{20}$alkyl, $C_2$-$C_{20}$alkenyl, $C_5$-$C_{12}$cycloalkyl, $C_1$-$C_4$alkyl—$C_5$-$C_{12}$cycloalkyl, phenyl-$C_1$-$C_4$alkyl, phenyl, naphthyl,

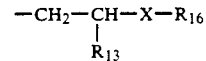

or —$CH_2C(CH_2$—O—$R_{16})_3$ or $R_6$, if $R_7$=H, can also be —$(CH_2)_f$—X—$R_{16}$ or $R_6$ and $R_7$, together with the N-bonding atom, form a 5- or 6-membered heterocyclic ring, $R_8$ and $R_9$ independently of one another are hydrogen, $C_1$-$C_{20}$alkyl, phenyl, —CO—$C_1$-$C_{20}$-alkyl, —CO—$C_2$-$C_{18}$ alkenyl, —CO—phenyl or —CO-naphthyl or together are =CH—$R_{17}$, $R_{10}$ is hydrogen, $C_1$-$C_{20}$alkyl, $C_2$-$C_{20}$alkenyl, $C_5$-$C_{12}$cycloalkyl, phenyl-$C_1$-$C_4$alkyl, phenyl, naphthyl, —CO—$C_1$-$C_{20}$alkyl, —CO-phenyl, —CO-naphthyl or

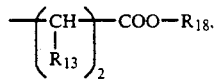

$R_{11}$ and $R_{12}$ independently of one another are hydrogen, $C_1$-$C_4$alkyl, cyclohexyl or phenyl, $R_{13}$ is hydrogen or methyl and $R_{13}'$ is hydrogen, methyl or phenyl, $R_{14}$ is $C_1$-$C_{20}$alkyl, $C_2$-$C_{20}$alkenyl, $C_5$-$C_{12}$cycloalkyl, phenyl-$C_1$-$C_4$alkyl, phenyl or naphthyl, the $R_{15}$ independently of one another are $C_1$-$C_4$alkyl, $R_{16}$ is hydrogen, —CO—$C_1$-$C_{20}$alkyl, —CO—$C_2$-$C_{20}$alkenyl, —CO-phenyl or —CO-naphthyl, $R_{17}$ is $C_1$-$C_{20}$alkyl, $C_2$-$C_{20}$alkenyl, $C_5$-$C_{12}$cycloalkyl, phenyl, naphthyl, 2-furyl,

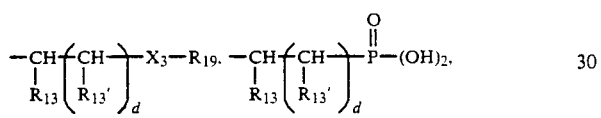

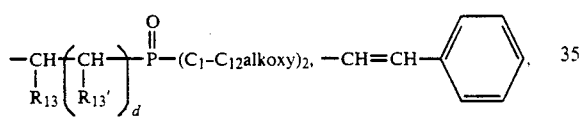

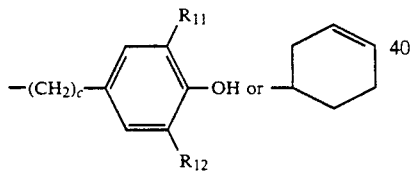

$R_{18}$ is hydrogen, $C_1$-$C_{20}$alkyl, $C_2$-$C_{20}$alkenyl, $R_{19}$ is $C_1$-$C_{20}$alkyl, $C_5$-$C_{12}$cycloalkyl, phenyl or —CH$_2$—COO—$C_{12}$-$C_{20}$alkyl, X and a are as defined above, $X_1$ is —O—, —S—, —NH—or —NR$_{14}$—, $X_2$ is a direct bond, —CH$_2$—, >CH—CH$_3$ or —S— and $X_3$ is —O—, —S—, —NH— or —NR$_{19}$—, b is 3 to 5, c is 0 to 2, d is 0 or 1, e is 2 to 10 and f is 2 to 6; with the proviso that A is not —OC$_1$-$C_{12}$alkyl, —NH$_2$, —NH-methyl, —NH-cyclohexyl,

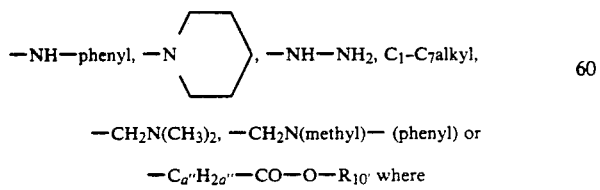

—CH$_2$N(CH$_3$)$_2$, —CH$_2$N(methyl)— (phenyl) or

—C$_{a''}$H$_{2a''}$—CO—O—R$_{10'}$ where a″ = 2 or 4 and R$_{10'}$ = hydrogen, methyl or ethyl, if R is hydrogen, chlorine, methyl or methoxy and R$_1$, $R_2$ and $R_3$ are hydrogen; or A, if n = 2, is —X′—C$_g$H$_{2g}$—X′—,

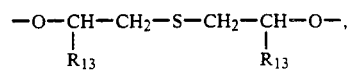

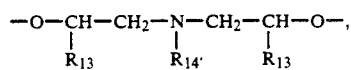

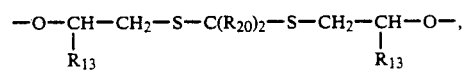

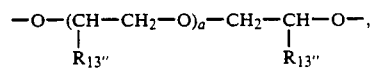

—OCH$_2$CH=CHCH$_2$O—, —OCH$_2$C≡CCH$_2$O—,

—O(CH$_2$)$_h$—NH—CO—X$_4$—OC—NH(CH$_2$)$_h$—O—,

—NH(CH$_2$)$_2$—X(CH$_2$)$_2$—O—,

—NH(CH$_2$CH$_2$NH)$_i$—CH$_2$CH$_2$NH—,

—NH(CH$_2$CH$_2$CH$_2$NH)$_i$CH$_2$CH$_2$CH$_2$NH—,

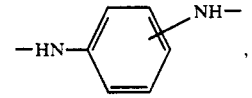

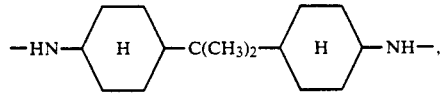

—NH(CH$_2$)$_h$—O—CO—X$_4$—OC—O—(CH$_2$)$_h$—NH—,

—NH—NH—,

—NH—NH—CO—X$_4$—OC—NH—NH—,

—NH—N=CH—X$_5$—CH=N—NH—,

—C$_p$H$_{2p}$—, —(CH$_2$)$_m$—X$_1$—(CH$_2$)$_m$—,

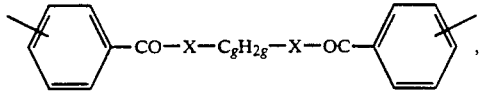

—C$_p$H$_{2p}$—CO—X—C$_g$H$_{2g}$—X—OC—C$_p$H$_{2p}$—,

—(CH$_2$)$_k$—O—CO—X$_4$—CO—O—(CH$_2$)$_k$—,

—CH=CH—CO—X—C$_g$H$_{2g}$—X—OC—CH=CH—,

—CH(OH)CH$_2$—, —CH(OH)CH(OH)—,

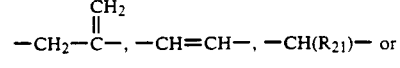

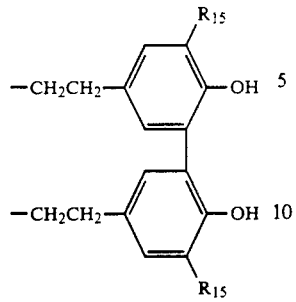

where X, $R_{13}$, $R_{15}$, a and f are as defined above, the X' independently of one another are —O— or —NH—, $R_{13}''$ is hydrogen or methyl and, if a =zero, can also be $C_2$-$C_{18}$alkyl or phenyl, $R_{14}'$ can have the same definition as $R_{14}$ or is hydrogen, the $R_{20}$ independently of one another are hydrogen, $C_1$-$C_{20}$alkyl, phenyl or together are a 5-12-membered cycloaliphatic ring, $R_{21}$ is $C_5$-$C_{12}$cycloalkyl, phenyl-$C_1$-$C_4$alkyl, phenyl or

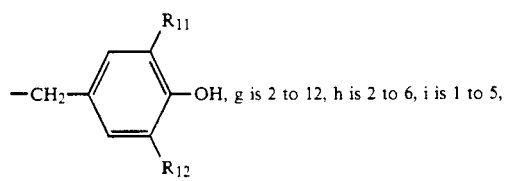, g is 2 to 12, h is 2 to 6, i is 1 to 5, k is 3 to 5, m is 1 or 2 and p is 1 to 10, $X_4$ is —$C_aH_{2a}$—, phenylene or —CH=CH— and $X_5$ is a direct bond, —(CH$_2$)$_3$— or —C(CH$_3$)$_2$—S—S—C(CH$_3$)$_2$—;

or A, if n = 3, is 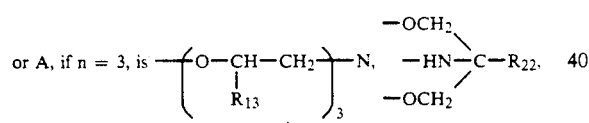

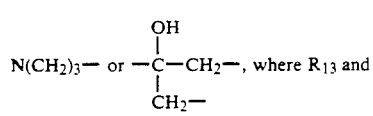

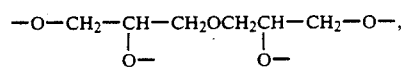

$R_{13}'$ are as defined above and $R_{22}$ is methyl or ethyl;

or A, if n = 4, is C(CH$_2$O)$_4$—,

—O—CH$_2$—CH—CH$_2$OCH$_2$CH—CH$_2$—O—,
        |                |
        O—              O—

$+$(OCH$_2$)$_3$—C—NH— or —(CH$_2$)$_2$NCH$_2$CH$_2$N(CH$_2$)$_2$—;

or A, if n = 5, is 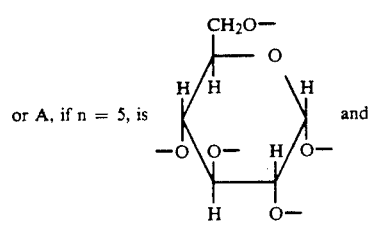 and if n = 6 is 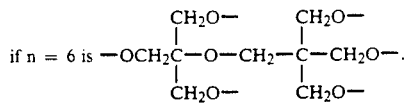.

Preferred compounds of the formula Ib are those in which R and $R_1$ independently of one another are hydrogen, $C_1$-$C_4$alkyl, $C_1$-$C_4$alkoxy or halogen, particularly chlorine, and $R_2$ and $R_3$ are hydrogen. According to a further preferred embodiment, compounds of the formula Ib are employed in which R is hydrogen, $C_1$-$C_4$alkyl, particularly methyl, $C_1$-$C_4$alkoxy, particularly methoxy, or chlorine and $R_1$, $R_2$ and $R_3$ are hydrogen.

Of particular interest are compounds of the formula Ib in which R is hydrogen, $C_1$-$C_4$alkoyl, $C_1$-$C_4$alkoxy or chlorine, $R_1$, $R_2$ and $R_3$ are hydrogen, n is 1 or 2, A, if n=1, is —OR$_5$, —NHR$_6$, —NH—NH—R$_8$, —NH—N=CH—R$_{17}$, $C_1$-$C_{17}$alkyl, $C_2$-$C_{17}$alkenyl,

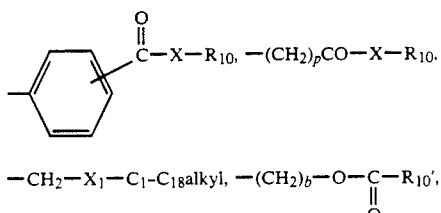

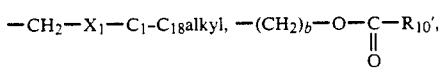

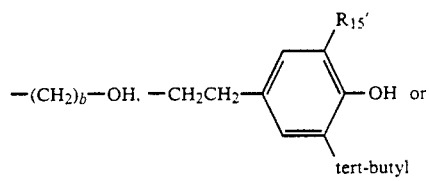

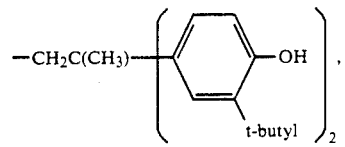

$R_{10}$ is hydrogen, $C_1$-$C_{18}$alkyl, $C_2$-$C_{18}$alkenyl, cyclohexyl, methylcyclohexyl or benzyl and $R_{10}'$ is $C_1$-$C_{17}$alkyl, $C_2$-$C_{17}$alkenyl or phenyl, $R_5$ is $C_1$-$C_{18}$alkyl, $C_2$-$C_{18}$alkenyl, cyclohexyl, methylcyclohexyl, benzyl,

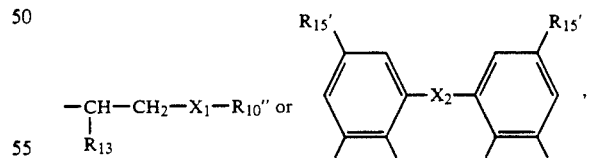

in which $R_{10}''$ is hydrogen, $C_1$-$C_{18}$alkyl or $C_2$-$C_{18}$alkenyl and the $R_{15}'$ independently of one another are methyl or tert-butyl, $R_6$ is $C_1$-$C_{18}$alkyl, $C_2$-$C_{18}$alkenyl, methylcyclohexyl, benzyl, —CH$_2$CH$_2$OH,

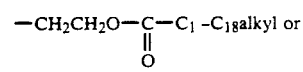

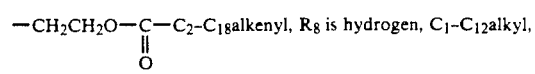

-continued

—CO—$C_1$-$C_{18}$alkyl or —CO—$C_2$-$C_{18}$alkenyl.

$R_{17}$ is $C_1$-$C_{11}$alkyl, $C_2$-$C_{11}$alkenyl, —$(CH_2)_m$—S—$C_1$-$C_{18}$alkyl or $$-(CH_2)_m-\overset{O}{\underset{\parallel}{P}}-(C_1\text{-}C_8\text{alkoxy})_2;$$

or A, if n = 2, is —O—$(CH_2)_g$—O—, —NH—$(CH_2)_g$—NH—,

—O—CH(R$_{13}$)—CH$_2$—S—CH$_2$—CH(R$_{13}$)—O—,

—O—CH(R$_{13}$)—CH$_2$—NH—CH$_2$CH(R$_{13}$)—O—,

—O—(CH(R$_{13}$)—CH$_2$O)$_{a'}$—CH$_2$CH(R$_{13}$)—O—where a' = zero to 5, or

—OCH$_2$—C(CH$_3$)$_2$CH$_2$—O—,

—NHCH$_2$CH$_2$—X—CH$_2$CH$_2$O—,

—NH(CH$_2$CH$_2$NH)$_i$—CH$_2$CH$_2$NH—,

—NH(CH$_2$CH$_2$CH$_2$NH)$_i$—CH$_2$CH$_2$CH$_2$—NH—,

—NH—C(CH$_3$)$_2$—CH$_2$O—,

—NHCH$_2$CH$_2$OC(O)(CH$_2$)$_a$C(O)OCH$_2$CH$_2$NH—,

—NH—NH—C(O)(CH$_2$)$_a$C(O)—NH—NH—,

—NH—N=CH—X$_5$—CH=N—NH—, —$(CH_2)_p$—,

[aromatic diacyl structure] —C(O)—X—(CH$_2$)$_g$—X—C(O)—,

—(CH$_2$)$_p$—C(O)—X—(CH$_2$)$_g$—X—C(O)—(CH$_2$)$_p$—,

—(CH$_2$)$_5$—O—C(O)—(CH$_2$)$_a$—C(O)—O—(CH$_2$)$_5$—,

—CH(R$_{21}$)— where R$_{21}$ = benzyl, phenyl or

[phenol structure with R$_{15}'$ substituents and —CH$_2$— link] —CH$_2$—...—OH or A is [biphenol structure with —CH$_2$CH$_2$— linkages and R$_{15}'$ substituents]

and a, b, g, i, m, p, X, X$_1$, X$_2$, X$_5$ and R$_{13}$ are as defined above.

Compounds of the formula Ib are also advantageous in which R is hydrogen, chlorine, methyl or methoxy and R$_1$, R$_2$ and R$_3$ are hydrogen, n is 1 or 2, A, if n=1, is —OR$_5$, —NHR$_6$, —NH—NH—R$_8$, —NH—N=CH—R$_{17}$, C$_8$-C$_{17}$alkyl, —(CH$_2$)$_p$—COOH, $$-(CH_2)_p-\overset{O}{\underset{\parallel}{C}}-O-C_3\text{-}C_{18}\text{alkyl}, -(CH_2)_b\text{OH},$$

—(CH$_2$)$_b$—OCO—C$_1$-C$_{18}$alkyl, —CH$_2$—S—C$_1$-C$_{18}$alkyl,

[phenyl]—COO—C$_1$-C$_{18}$alkyl or

—CH$_2$CH$_2$—[phenyl with R$_{15}'$ and tert-butyl]—OH where R$_5$ is C$_{13}$-C$_{18}$alkyl, cyclohexyl, methylcyclohexyl, benzyl or

[bisphenol structure with R$_{15}'$ substituents and X$_2$ linker], R$_6$ is C$_2$-C$_{18}$alkyl, benzyl, —(CH$_2$)$_f$—OH or —CH$_2$CH$_2$O—CO—C$_1$-C$_{18}$alkyl, R$_8$ is —CO—C$_1$-C$_{18}$alkyl or —COCH=CH$_2$, the R$_{15}'$ independently of one another are methyl or tert-butyl, R$_{17}$ is C$_1$-C$_{11}$alkyl, —(CH$_2$)$_m$—S—C$_1$-C$_{18}$alkyl or $$-(CH_2)_m-\overset{O}{\underset{\parallel}{P}}-(C_1\text{-}C_4\text{alkoxy})_2, \text{ or A, if n = 2,}$$

is —O—(CH$_2$)$_g$—O—, —NH—(CH$_2$)$_g$—NH—,

—OCH$_2$CH$_2$SCH$_2$CH$_2$O—, —O(CH$_2$CH$_2$O)$_c$—CH$_2$CH$_2$—O—,

—OCH$_2$C(CH$_3$)$_2$CH$_2$O—, —NHCH$_2$CH$_2$OCH$_2$CH$_2$O—,

—NHCH$_2$CH$_2$OC(O)(CH$_2$)$_a$C(O)OCH$_2$CH$_2$NH—,

—NH—NH—C(O)(CH$_2$)$_a$C(O)—NH—NH—,

—NH—N=CH—C(CH$_3$)$_2$—S—S—C(CH$_3$)$_2$—CH=N—NH— or

—(CH$_2$)$_p$—, where a, b, c, f, g, m, p and X$_2$ are as defined above.

Particularly preferred compounds of the formula Ib are those in which R is chlorine, methyl or methoxy and in particular hydrogen, R$_1$, R$_2$ and R$_3$ are hydrogen, n is 1 or 2, A, if n=1, is —OR$_5$, —NHR$_6$, —NH—NH—R$_8$, —NH—N=CH—R$_{17}$, C$_8$-C$_{17}$alkyl, —(CH$_2$)$_{p'}$—CO—O—C$_8$-C$_{18}$alkyl where p'=2 to 6, —(CH$_2$)$_b$—OH, —(CH$_2$)$_b$—OCO—C$_8$-C$_{18}$alkyl, —CH$_2$—S—C$_8$-C$_{18}$-alkyl,

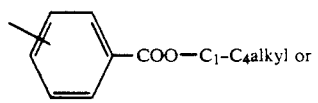

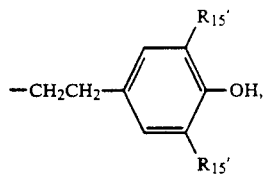

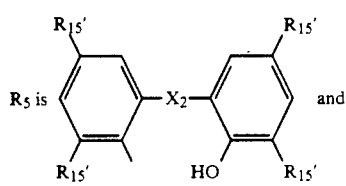

in particular $C_{13}$-$C_{18}$alkyl, $R_6$ is $C_8$-$C_{18}$alkyl,

—$(CH_2)_{f'}$—OH where $f' = 2$ or $3$ or

—$CH_2CH_2OCO$—$C_8$-$C_{18}$alkyl, $R_8$ is —$CO$—$C_8$-$C_{18}$alkyl or

—$COCH=CH_2$, $R_{17}$ is $C_8$-$C_{11}$alkyl,

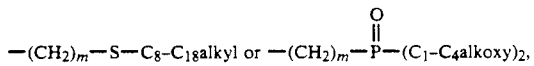

or A, if $n=2$, is —$O(CH_2)_gO$—, —$NH(CH_2)_gNH$—, —$OCH_2CH_2SCH_2CH_2O$—, —$O(CH_2CH_2O)_cCH_2CH_2O$—, —$OCH_2C(CH_3)_2CH_2O$—, —$NHCH_2CH_2OCH_2CH_2O$—, —$NHCH_2CH_2OCO$—$(CH_2)_{a'}$—$OCOCH_2CH_2NH$— or —$NH$—$NHCO$—$(CH_2)_{a'}$—$CONH$—$NH$— where $a''=2$ to $8$, —$NH$—$N=CH$—$C(CH_3)_2$—$S$—$S$—$C(CH_3)_2$—$CH=N$—$NH$— or —$(CH_2)_{p''}$— where $p''=5-10$, b is 3 to 5, particularly 5, $X_2$ is a direct bond or $>CH$—$CH_3$ and $R_{15}'$, c, g and m are as defined above. Very particularly preferred compounds of the formula Ib are those in which R, $R_1$, $R_2$ and $R_3$ are hydrogen, n is 1 or 2, A, if $n=1$, is $C_8$-$C_{17}$alkyl, —$OR_5$, —$NHR_6$ or —$NH$—$NH$—$CO$—$C_8$-$C_{17}$alkyl, $R_5$ is $C_{13}$-$C_{18}$alkyl and $R_6$ is $C_8$-$C_{18}$alkyl, or A, if $n=2$, is —$O(CH_2)_g$—$O$—, —$NH(CH_2)_gNH$—, —$OCH_2C(CH_3)_2CH_2O$—, —$NH$—$NHCO$—$CH_2CH_2$—$OCNH$—$NH$— or —$(CH_2)_{p''}$— where $p''=5$ to $10$, where g is as defined above.

The invention further relates to the use of compounds of the formula I or Ib for stabilising organic materials against oxidative, thermal and/or actinic degradation. The use of compounds of the formula I or Ia as stabilisers in lubricants, metal processing fluids, hydraulic fluids or in natural, semi-synthetic or synthetic polymers, preferably halogen-free polymers, is preferred.

The invention accordingly also comprises a method for stabilising organic materials, particularly lubricants, metal processing fluids, hydraulic fluids or natural, semi-synthetic or synthetic polymers, by adding compounds of the formula I or Ib to the organic material as stabilisers or applying them to this.

The compounds of the formula I or Ib can be prepared in a manner known per se, for example as follows:

A) Esters according to the definition can be obtained, for example, by reaction of α-cyanophenylacetic acid esters of the formula II

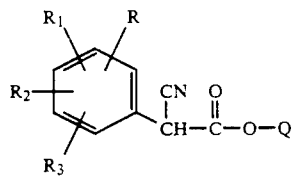

Q = for example, $C_1$-$C_6$alkyl, particularly methyl, with suitable alcohols HO—$[A]_n$ in the presence of catalytic amounts of a strong acid, such as methane- or p-toluenesulfonic acid. Higher esters are advantageously prepared by acid-catalysed transesterification.

Esters of the formula I or Ib in which A is the radical of a bisphenol can also be prepared, for example, by reacting a benzyl cyanide of the formula III

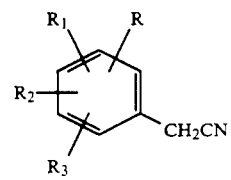

under basic conditions with a cyclic carbonic acid ester of the appropriate bisphenol.

B) Amides can be obtained analogously to A) by reaction of α-cyanophenylacetic acid esters of the formula II with amines $H_2N$—$[A]_n$ or aminoalcohols in a suitable solvent, such as ethanol, toluene or xylenes, or in the melt. Amidoesters can be prepared by reaction of α-cyanophenylacetic acid esters of the formula II with suitable aminoalcohols and subsequent esterification, for example with an acid chloride in the presence of a base, such as pyridine.

C) Hydrazides can likewise be prepared analogously to A) by reaction of α-cyanophenylacetic acid esters of the formula II with hydrazines, for example those of the formula $H_2N$—$NH$—$[A]_n$, or by reaction of an α-cyanophenylacetic acid hydrazide of the formula IV

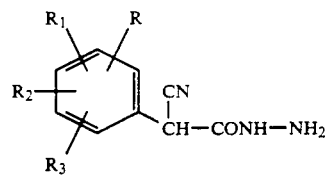

with suitable acid chlorides or aldehydes.

D) α-Ketophenylacetonitriles or α-cyanophenylacetic acids (A=—OH) can be obtained, for example, by base-catalysed reaction of benzyl cyanides of the formula III with carboxylic acid esters Q—O—CO—$[A]_n$ or dimethyl carbonate. Suitable bases are in particular alkali metal alkoxides and hydrides. The reaction is advantageously carried out in an organic solvent, for example alcohols, aliphatic or aromatic hydrocarbons, such as n-pentane, toluene or xylenes, dimethyl sulfoxide or aliphatic or cyclic ethers, such as methyl isopropyl ether and tetrahydrofuran. The cyanoketocarboxylic acid esters obtained in the reaction of polybasic carboxylic acid esters (n=2, 3 or 4) with only one equivalent of benzyl cyanide can be further reacted, for example esterified with higher alcohols.

By reaction of benzyl cyanides of the formula III with lactones, α-cyanoketoalcohols are obtained which can also be further esterified, for example with an acid chloride in the presence of a base, such as pyridine.

E) Dimeric compounds of the formula I

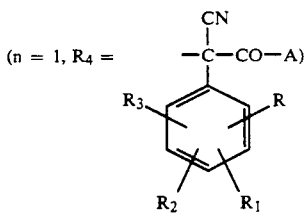

can be obtained in a manner known per se by oxidative coupling of compounds of the formula V

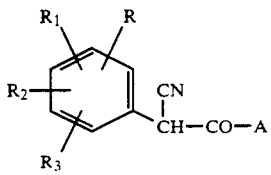

(V) (cf. for example J. Org. Chem., 36, 3160–3168 (1971) and DE-A 2 033 910). A in this case is preferably the radical of a monohydric alcohol, amine or ketone.

Compounds of the formula I having functional groups, such as hydroxyl groups, primary or secondary amino groups or carboxamide groups, can be converted in a manner known per se into other derivatives according to the definition, for example by esterification, N-alkylation and the like.

The alcohols, amines, aminoalcohols, hydrazines, carboxylic acid esters, acid chlorides, aldehydes and lactones used as starting materials and the compounds of the formulae II–V are known per se or can be prepared in a manner known per se.

The following examples illustrate the invention in greater detail, without wishing to restrict it to the examples. In these examples and in the remaining description and in the patent claims, parts and percentages are parts by weight and percentages by weight, if not stated otherwise. EA is elemental analysis.

PREPARATION EXAMPLES 1–39

A) Esters 1. 39.4 g of 1,6-hexanediol and 133.9 g of methyl α-cyanophenylacetate are treated with 0.32 g of methanesulfonic acid and the mixture is then stirred at 150° C. under a slight vacuum (about 200 mbar) for 12 hours. The excess methyl ester (20.2 g) is then distilled off at a bath temperature of 150° C. and a pressure of about $2 \times 10^{-3}$ mbar. The still warm oily residue is diluted with 200 ml of diethyl ether, filtered and then placed in the refrigerator. The crystallised solid is filtered off with suction, washed with 200 ml of cold diethyl ether and dried. 111.4 g (82.6% of theory) of the compound No. 3 given in the following Table I are thus obtained in the form of a white solid of melting range 60°–65° C.

The compounds Nos. 1, 2, 4–8, 37, 38, 39 and 40 given in the following Table I are prepared in an analogous manner, the corresponding p-methoxyphenyl, p-chlorophenyl or p-methylphenyl derivative being employed instead of the methyl α-cyanophenylacetate in the case of compounds Nos. 37, 38 and 39.

2. 0.65 g of sodium hydride (55%) are suspended in 10 ml of dimethyl sulfoxide and 12 ml of tetrahydrofuran. 1.9 g of benzyl cyanide are then added dropwise at −5° C. 6.5 g of the cyclic carbonate of 4,4′,6,6′-tetra-t-butyl-2,2′-bisphenol are then added, and the mixture is stirred at room temperature for 23 hours. 600 ml of ice-water are then added, the mixture is acidified with 3 ml of conc. HCl and the precipitate is filtered off with suction and recrystallised from n-hexane. 6.3 g (76% of theory) of compound No. 34 are thus obtained in the form of a white solid of melting point 189°–192° C.

Compound No. 35 is prepared in an analogous manner.

B) Amides 1. 17.5 g of methyl α-cyanophenylacetate and 5.8 g of 1,6-diaminohexane are heated to reflux in 75 ml of xylene for 3 hours. The reaction mixture is then cooled, diluted with 100 ml of petroleum ether, and the solid is filtered off with suction, washed with cold methanol and dried. The crude diamide obtained (17.0 g = 84.5% of theory) is recrystallised from 80 ml of acetic acid. 12.0 g (59.6% of theory) of compound No. 10 are thus obtained in the form of a white solid of m.p. 185°–190° C.

Compounds Nos. 9, 11 and 12 are prepared in an analogous manner.

2. 6.12 g of compound No. 12 are dissolved in 30 ml of pyridine. 9.45 ml of palmitoyl chloride are then added, and the mixture is stirred at room temperature for 3 hours. 200 ml of water are then added, and the precipitate is filtered off with suction, washed with water and dissolved in methylene chloride. The solution obtained is dried over magnesium sulfate and evaporated, and the residue is recrystallised from acetonitrile. 11.6 g (87% of theory) of compound No. 13 are thus obtained in the form of a white solid of m.p. 81°–84° C. Compounds Nos. 14 and 15 are prepared in an analogous manner.

C) Hydrazides 1. 8.76 g of α-cyanophenylacetic acid hydrazide are dissolved in 50 ml of pyridine. 13.75 g of palmitoyl chloride are then added, and the mixture is stirred at room temperature for 1 hour. 400 ml of ice-water are then added, and the precipitate which is deposited is filtered off with suction, washed with water and then recrystallised first from acetonitrile/toluene and then from toluene. 14.2 g (69% of theory) of compound No. 16 are obtained in the form of a white solid of m.p. 141°–143° C.

Compounds Nos. 17 and 41 are prepared in an analogous manner.

2. 5.84 g of α-cyanophenylacetic acid hydrazide are suspended in 50 ml of methylene chloride. 3.44 g of bis-2,2′-thioisobutyraldehyde are then added, and the mixture is stirred at room temperature under nitrogen for 3 hours. The water of reaction liberated is dried off with magnesium sulfate, and the mixture is filtered and evaporated. The residue is dissolved in 50 ml of toluene and the solution is then precipitated with 250 ml of n-hexane. This operation is repeated once, whereupon 5.9 g (68% of theory) of compound No. 20 are obtained in the form of white solid of m.p. 100°–104° C.

Compound Nos. 18, 19 and 21 are prepared in an analogous manner.

D) Ketones 1. 17.8 g of benzyl cyanide and 17.8 g of dimethyl sebacate are dissolved in 10 ml of tetrahydrofuran and the solution is added dropwise at −3° C. to +3° C. to a suspension of 6.7 g of sodium hydride (55% in oil) in 60 ml of tetrahydrofuran and 50 ml of dimethyl sulfoxide. The mixture is then stirred at room temperature for 5 hours and then diluted with 1200 ml of ice-water and 20 ml of hydrochloric acid. The solid which is deposited is extracted with methylene chloride, and the extract is washed three times with water, dried over magnesium sulfate and evaporated. After crystallising from toluene/n-hexane three times, 17.9 g (66% of theory) of compound No. 23 are obtained in the form of a white solid of m.p. 70°-74° C.

Compounds Nos. 22, 27-32 and 36 are prepared in an analogous manner.

2. 5.25 g of sodium hydride (55%) are suspended in 45 ml of dimethyl sulfoxide and 55 ml of tetrahydrofuran. 14.1 g of ε-caprolactone and 14.1 g of benzyl cyanide are then simultaneously added dropwise at −3° C. After stirring at room temperature for 5.5 hours, 800 ml of ice-water are added, and the mixture is acidified with 20 ml of conc. HCl. The oil which is deposited is extracted with methylene chloride, and the extract is washed with water and dried over magnesium sulfate. After evaporating the solvent, the residue is distilled at $6 \times 10^{-3}$ mbar. 13.2 g (47% of theory) of the virtually pure compound No. 24 pass over between 138°-173° C.; m.p. 97°-102° C. The compound solidifies after cooling.

6.95 g of the above ketoalcohol (compound No. 24) are dissolved in 30 ml of pyridine and treated with 8.5 g of palmitoyl chloride. After stirring at room temperature for 22 hours, 300 ml of ice-water are added, and the mixture is extracted with diethyl ether. 4.6 g (33% of theory) of compound No. 25 are obtained from the residue, after evaporating the diethyl ether, by chromatography on silica gel (methylene chloride/hexane=4:1) and crystallisation from acetonitrile; m.p. 36°-41° C.

3. 10.9 g of sodium methoxide are dissolved in 50 ml of methanol. 17.6 g of benzyl cyanide and 36.0 g of dimethyl glutarate are then simultaneously added dropwise. After refluxing for 5.5 hours, 800 ml of ice-water and 30 ml of acetic acid are added, and the mixture is extracted with diethyl ether. 15.5 g of the pure ketomethyl ester are obtained from the residue, after evaporating the diethyl ether, by distillation at $4 \times 10^{-3}$ mbar/140°-147° C. 10.8 g of this methyl ester are stirred in a slight vacuum (about 200 mbar) for 4.5 hours with 9.8 g of n-octadecanol and 0.2 g of p-toluenesulfonic acid. 8.9 g (46% of theory) of compound No. 26 of m.p. 62°-64° C. are obtained by chromatography on silica gel (methylene chloride/hexane=3:1) and crystallisation from acetonitrile.

E) Dimers 17.5 g of methyl α-cyanophenylacetate are added at room temperature to a solution of 2.3 g of sodium in 50 ml of absolute methanol. 12.4 g of iodine are then added in portions with continuous stirring, and the mixture is stirred for a further 30 minutes. The pale yellow solution obtained is diluted with 100 ml of methylene chloride, washed with water and dried over sodium sulfate. The residue is recrystallised twice from methanol after evaporation. 6.8 g (39% of theory) of compound No. 33 are obtained as a diastereomer mixture of m.p. 149°-155° C.

The structure and physical data of compounds Nos. 1-41 are collated in Table I which follows.

TABLE I

| No | Compound | m.p. °C. | EA: C (calculated/found) | H | N |
|---|---|---|---|---|---|
| 1 | ⟨phenyl⟩−CH(CN)−CO$_2$−C$_{18}$H$_{37}$ | 46-48 | 78.40 / 78.30 | 10.48 / 10.47 | 3.39 / 3.26 |
| 2 | [⟨phenyl⟩−CH(CN)−CO$_2$−(CH$_2$)$_2$−]$_2$ | 81-83 | 70.20 / 70.09 | 5.36 / 5.46 | 7.44 / 7.64 |
| 3 | [⟨phenyl⟩−CH(CN)−CO$_2$−(CH$_2$)$_3$−]$_2$ | 60-65 | 71.27 / 71.31 | 5.98 / 5.94 | 6.93 / 7.00 |
| 4 | [⟨phenyl⟩−CH(CN)−CO$_2$−(CH$_2$)$_6$−]$_2$ | 39-41 | 73.74 / 73.78 | 7.43 / 7.57 | 5.73 / 5.70 |
| 5 | [⟨phenyl⟩−CH(CN)−CO$_2$−CH$_2$−]$_2$C(CH$_3$)$_2$ | Oil | 70.75 / 70.45 | 5.68 / 5.70 | 7.18 / 7.08 |

TABLE I-continued

| No | Compound | m.p. °C. | EA: C (calculated/found) | H | N |
|---|---|---|---|---|---|
| 6 | [Ph-CH(CN)-CO₂-CH₂-CH₂-]₂S | 54–58 | 64.69 / 64.44 | 4.94 / 4.98 | 6.86 / 6.72 |
| 7 | [Ph-CH(CN)-CO₂-CH₂-CH₂-]₂O | Oil | 67.34 / 67.11 | 5.14 / 5.19 | 7.14 / 7.07 |
| 8 | [Ph-CH(CN)-CO₂-CH₂-CH₂-O-]₂(CH₂)₂ | Oil | 66.05 / 66.04 | 5.54 / 5.66 | 6.42 / 6.24 |
| 9 | Ph-CH(CN)-CO-NH-C₁₆H₃₃ | 87–89 | 78.07 / 77.82 | 10.48 / 10.44 | 7.28 / 7.26 |
| 10 | [Ph-CH(CN)-CO-NH-(CH₂)₃-]₂ | 185–190 | 71.62 / 71.56 | 6.51 / 6.60 | 13.92 / 13.97 |
| 11 | [Ph-CH(CN)-CONH-(CH₂)₆-]₂ | 132–134 | 74.04 / 73.84 | 7.87 / 8.03 | 11.51 / 11.56 |
| 12 | Ph-CH(CN)-CONH-CH₂-CH₂-OH | 108–110 | 64.69 / 64.75 | 5.92 / 5.95 | 13.72 / 13.78 |
| 13 | Ph-CH(CN)-CONH-(CH₂)₂O-C(=O)-C₁₅H₃₁ | 81–84 | 73.26 / 73.20 | 9.56 / 9.59 | 6.33 / 6.09 |
| 14 | [Ph-CH(CN)-CONH-(CH₂)₂O-C(=O)-(CH₂)₂-]₂ | 143–148 | 64.85 / 64.70 | 5.83 / 5.87 | 10.80 / 11.27 |
| 15 | [Ph-CH(CN)-CONH-(CH₂)₂O-C(=O)-(CH₂)₄-]₂ | Oil | 66.88 / 66.16 | 6.67 / 6.71 | 9.75 / 9.58 |
| 16 | Ph-CH(CN)-CONH-NH-COC₁₅H₃₁ | 141–143 | 72.60 / 72.63 | 9.50 / 9.52 | 10.16 / 10.01 |

TABLE I-continued
| No | Compound | m.p. °C. | EA: C (calculated/found) | H | N |
|---|---|---|---|---|---|
| 17 | 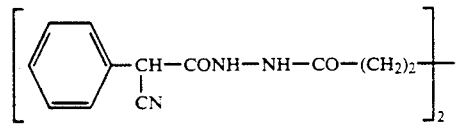 | 228–230 decomposition | 62.60 62.24 | 5.25 5.35 | 18.25 18.09 |
| 18 | 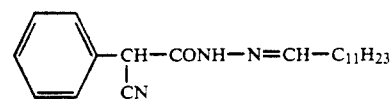 | 100–103 | 73.86 73.94 | 9.15 9.18 | 12.30 12.50 |
| 19 | 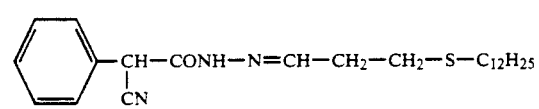 | 83–85 | 69.35 69.33 | 8.97 8.97 | 10.11 10.14 |
| 20 | 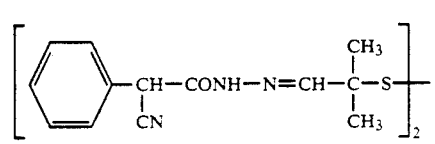 | 100–104 | 59.98 60.01 | 5.42 5.57 | 16.14 16.06 |
| 21 | 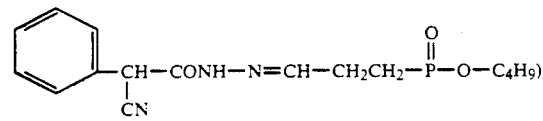 | Oil | 58.96 58.72 | 7.42 7.63 | 10.31 9.83 |
| 22 | 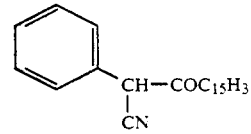 | 69–72 | 81.07 80.90 | 10.49 10.56 | 3.94 3.83 |
| 23 | 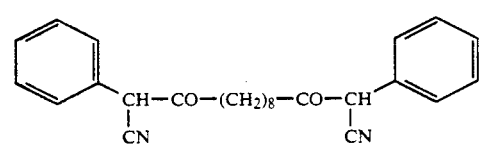 | 70–74 | 77.97 77.76 | 7.05 7.17 | 6.99 6.94 |
| 24 | 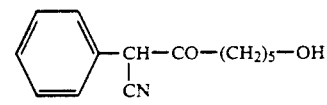 | 97–102 | 72.70 72.71 | 7.41 7.23 | 6.06 6.19 |
| 25 | 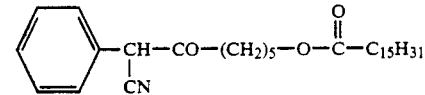 | 36–41 | 76.71 76.67 | 10.09 10.00 | 2.98 2.99 |
| 26 | 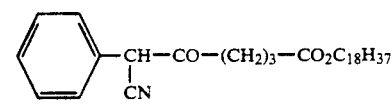 | 62–64 | 76.97 77.00 | 10.21 10.23 | 2.90 3.16 |
| 27 | 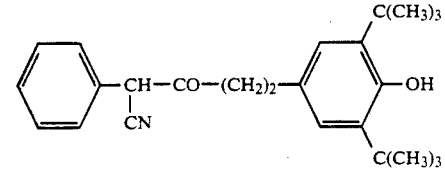 | 97–97 | 79.54 79.48 | 8.28 8.28 | 3.71 3.65 |

TABLE I-continued

| No | Compound | m.p. °C. | EA: | C | H | N |
|---|---|---|---|---|---|---|
| | | | | (calculated/found) | | |
| 28 | Ph-CH(CN)-CO-(CH₂)₂-[3-C(CH₃)₃, 4-OH, 5-CH₃-C₆H₂] | 105–107 | | 78.77<br>78.80 | 7.51<br>7.52 | 4.18<br>4.27 |
| 29 | Ph-CH(CN)-CO-O-C₆H₄-4-CO₂CH₃ | 98–100 | | 73.11<br>72.96 | 4.69<br>4.74 | 5.02<br>4.94 |
| 30 | Ph-CH(CN)-CO-O-C₆H₄-3-CO₂CH₃ | 90–92 | | 73.11<br>72.86 | 4.69<br>4.76 | 5.02<br>5.04 |
| 31 | Ph-CH(CN)-CO-O-C₆H₄(1,3)-O-CO-CH(CN)-Ph | 105–118 | | 79.11<br>78.71 | 4.43<br>4.75 | 7.69<br>7.42 |
| 32 | Ph-CH(CN)-CO-CH₂-S-C₁₆H₃₃ | 59–62 | | 75.13<br>75.03 | 9.94<br>9.48 | 3.37<br>3.59 |
| 33 | Ph-C(CN)(CO₂CH₃)-C(CN)(CO₂CH₃)-Ph | 149–155 | | 68.96<br>69.04 | 4.63<br>4.68 | 8.04<br>8.06 |
| 34 | Bis-phenol [3,3',5,5'-tetra-t-butyl-2,2'-biphenyldiol] mono ester of Ph-CH(CN)-COOH | 189–192 | | 80.25<br>80.24 | 8.55<br>8.47 | 2.53<br>2.59 |
| 35 | Bis-phenol methylene-bridged [3,3',5,5'-tetra-t-butyl-2,2'-methylenediphenol] mono ester of Ph-CH(CN)-COOH | 158–162 | | 80.51<br>80.50 | 8.84<br>8.92 | 2.41<br>2.31 |

TABLE I-continued

| No | Compound | m.p. °C. | EA: C H N (calculated/found) |
|---|---|---|---|
| 36 | NC-CH(C₆H₅)-C(O)-(CH₂)₁₀-C(O)-CH(CN)-C₆H₅ | 55–78 | 78.47 7.53 6.54 / 78.44 7.66 6.28 |
| 37 | [CH₃O-C₆H₄-CH(CN)-CO₂-(CH₂)₃-]₂ | Oil | 67.22 6.08 6.03 / 67.10 6.13 6.39 |
| 38 | [CH₃-C₆H₄-CH(CN)-CO₂-(CH₂)₃-]₂ | 56–63 | 72.20 6.53 6.48 / 72.06 6.56 6.22 |
| 39 | [Cl-C₆H₄-CH(CN)-CO₂-(CH₂)₃-]₂ | Oil | 60.90 4.68 5.92 / 60.96 4.69 5.94 |
| 40 | C₆H₅-CH(CN)-CONHCH₂CH₂OCH₂CH₂OC(O)-CH(CN)-C₆H₅ | Oil | 67.51 5.41 10.74 / 67.36 5.49 10.68 |
| 41 | C₆H₅-CH(CN)-CONHNHCO-CH=CH₂ | 179–183 | 62.87 4.84 18.33 / 62.50 4.87 18.24 |

USE EXAMPLES: STABILISATION OF POLYPROPYLENE.

1.3 kg of polypropylene powder (melt flow index 3.2 g/10 min., measured at 230° C. using 2.16 kg) are mixed with 0.05% calcium stearate, 0.05% IRGANOX® 1010 and 0.05% of the processing stabilisers of the formula I given in Table II. The mixture is extruded at 100 rpm in an extruder having a cylinder diameter of 20 mm and a length of 20 d=400 mm, the 3 heating zones being set to 260° C., 270° C. and 280° C. The extrudate is drawn through a water bath for cooling and then granulated. The melt flow index is measured (at 230° C. using 2.16 kg) after these three extrusions. Polypropylene is extruded in an analogous manner without processing stabilisers. The results are collated in Table II which follows.

The increase in the melt flow index is a measure of the chain degradation of the polymer and thus of the stabiliser effect.

TABLE II

| Compound No. | Melt flow index after 3 extrusions g/10 min. at 230° C. using 2.16 kg |
|---|---|
| without stabiliser | 17.8 |
| 1 | 8.8 |
| 2 | 6.4 |
| 3 | 6.4 |
| 4 | 6.4 |
| 5 | 6.5 |
| 6 | 6.8 |
| 7 | 7.2 |
| 8 | 6.9 |
| 9 | 8.5 |
| 10 | 6.4 |
| 11 | 6.9 |
| 13 | 8.7 |
| 14 | 7.7 |
| 15 | 8.3 |
| 16 | 6.9 |
| 17 | 5.8 |
| 18 | 7.0 |
| 19 | 8.4 |
| 20 | 4.9 |
| 21 | 8.8 |
| 22 | 7.7 |
| 23 | 6.6 |
| 25 | 8.3 |
| 26 | 7.9 |
| 27 | 7.4 |
| 28 | 6.6 |
| 29 | 7.3 |
| 30 | 7.2 |
| 31 | 6.6 |
| 32 | 7.2 |
| 33 | 7.1 |
| 36 | 8.4 |
| 37 | 7.4 |
| 38 | 8.3 |
| 39 | 8.8 |
| 40 | 7.3 |

What is claimed is:

1. A stabilized composition which comprises
   (a) a polymer, functional fluid or lubricant, subject to thermal, oxidative or actinic degradation, and
   (b) an effective stabilizing amount of at least one compound of formula I

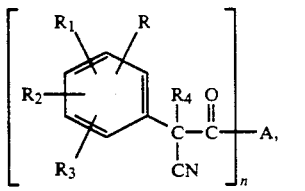

in which R is hydrogen, —OH, halogen, $C_1$-$C_{20}$alkyl, $C_2$-$C_{20}$alkenyl, $C_5$-$C_{12}$cycloalkyl, $C_1$-$C_4$alkyl-$C_5$-$C_{12}$cycloalkyl, phenyl, naphthyl, $C_1$-$C_{20}$alkoxy, phenyloxy, naphthyloxy, —S—$C_1$-$C_{20}$alkyl, —S—phenyl, —S—naphthyl, —O—CO—$C_1$-$C_{20}$alkyl, —O—CO—phenyl, —O—CO—naphthyl, —COOH, —COO—$C_1$-$C_{20}$alkyl, —COO—$C_2$-$C_{20}$alkenyl, —COO—phenyl, —COO—naphthyl, —CONR'R", —CO—$C_1$-$C_{20}$alkyl, —CO—phenyl, —CO—naphthyl, —NHCO—$C_1$-$C_{20}$alkyl, —NHCO—$C_2$-$C_{20}$alkenyl, —NHCO—phenyl or —NHCO—naphthyl, $R_1$ can have the same meaning as R, $R_2$ is hydrogen, halogen or $C_1$-$C_4$alkyl and $R_3$ is hydrogen or halogen, or two radicals R, $R_1$, $R_2$ or $R_3$ bonded to one another in the ortho-position together form tetramethylene or —CH=CH—CH=CH—, where the remaining two radicals of R, $R_1$, $R_2$ and $R_3$ are hydrogen, R' and R" independently of one another are hydrogen, $C_1$-$C_{20}$alkyl, $C_2$-$C_{20}$alkenyl, phenyl or naphthyl or, together with the bonding N atom, form a 5- or 6-membered heterocyclic ring, a is zero to 10, n is 1 to 6, X is —O— or —NH—,
$R_4$ is hydrogen, or, when n=1, $R_4$ is also a group

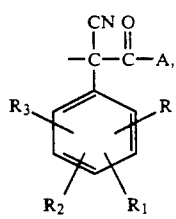

A, when n=1, is —OH, —$OR_5$, —$NR_6R_7$, —NH—$NR_8R_9$, $C_1$-$C_{30}$alkyl, $C_2$-$C_{30}$alkenyl, $C_5$-$C_{12}$cycloalkyl, $C_1$-$C_4$alkyl-$C_5$-$C_{12}$cycloalkyl

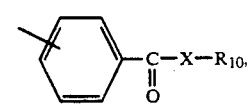

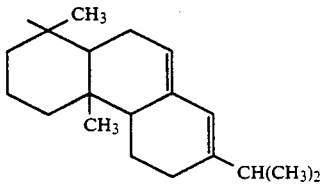

or the corresponding dihydro or tetrahydro derivative, —$C_aH_{2a}$—CO—X—$R_{10}$, —$C_bH_{2b}$—OCO—$R_{10}$, —$C_bH_{2b}$—OH,

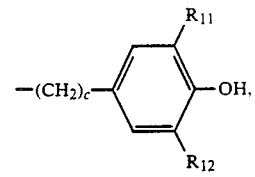

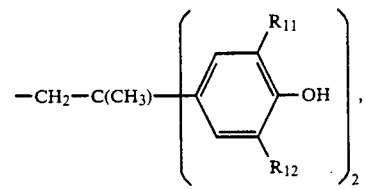

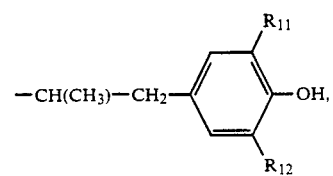

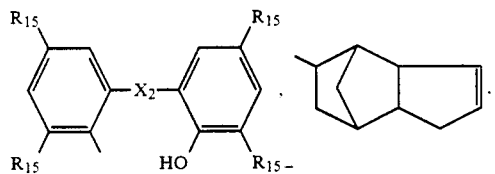

where $R_5$ is $C_1$-$C_{30}$alkyl, $C_2$-$C_{30}$alkenyl, $C_5$-$C_{12}$cycloalkyl, $C_1$-$C_4$alkyl-$C_5$-$C_{12}$cycloalkyl, phenyl-$C_1$-$C_4$alkyl, phenyl, naphthyl, biphenyl, the radical of a terpene alcohol or a radical of the formulae

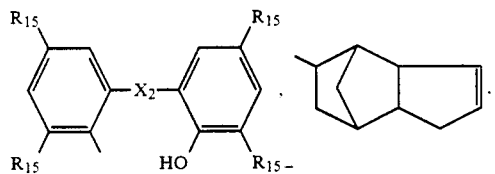

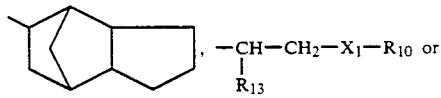

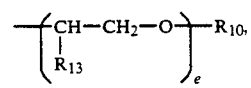

$R_6$ and $R_7$ independently of one another are hydrogen, $C_1$-$C_{20}$alkyl, $C_2$-$C_{20}$alkenyl, $C_5$-$C_{12}$cycloalkyl, $C_1$-$C_4$alkyl-$C_5$-$C_{12}$cycloalkyl, phenyl-$C_1$-$C_4$alkyl, phenyl, naphthyl,

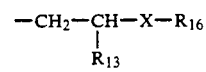

or —$CH_2C(CH_2$—$O$—$R_{16})_3$ or $R_6$, if $R_7$=H, can also be —$(CH_2)_f$—X—$R_{16}$ or $R_6$ and $R_7$, together with the N bonding atom, form a 5- or 6-membered heterocyclic ring, $R_8$ and $R_9$ independently of one another are hydrogen, $C_1$-$C_{20}$alkyl, phenyl, —CO—$C_1$-$C_{20}$alkyl, —CO—$C_2$-$C_{18}$alkenyl, —CO-phenyl or —CO-naphthyl or together are =CH—$R_{17}$, $R_{10}$ is hydrogen, $C_1$-$C_{20}$alkyl, $C_2$-$C_{20}$alkenyl, $C_5$-$C_{12}$cycloalkyl, phenyl-$C_1$-$C_4$alkyl, phenyl, naphthyl, —CO—$C_1$-$C_{20}$alkyl, —CO-phenyl, —CO-naphthyl or

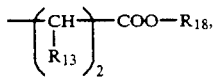

$R_{11}$ and $R_{12}$ independently of one another are hydrogen, $C_1$-$C_4$alkyl, cyclohexyl or phenyl, $R_{13}$ is hydrogen or methyl and $R_{13}'$ is hydrogen, methyl or phenyl, $R_{14}$ is $C_1$-$C_{20}$alkyl, $C_2$-$C_{20}$alkenyl, $C_5$-$C_{12}$cycloalkyl, phenyl-$C_1$-$C_4$alkyl, phenyl or naphthyl, the $R_{15}$ independently of one another are $C_1$-$C_4$alkyl, $R_{16}$ is hydrogen, —CO—$C_1$-$C_{20}$alkyl, —CO—$C_2$-$C_{20}$alkenyl, —CO-phenyl or —CO-naphthyl, $R_{17}$ is $C_1$-$C_{20}$alkyl, $C_2$-$C_{20}$alkenyl, $C_5$-$C_{12}$cycloalkyl, phenyl, naphthyl, 2-furyl,

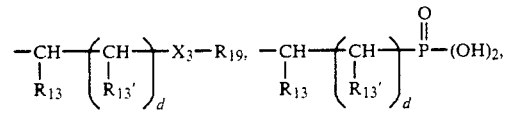

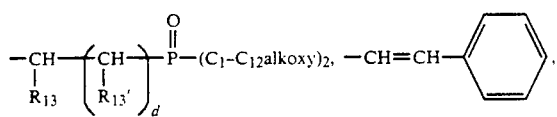

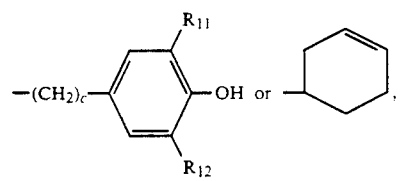

$R_{18}$ is hydrogen, $C_1$-$C_{20}$alkyl or $C_2$-$C_{20}$alkenyl, $R_{19}$ is $C_1$-$C_{20}$alkyl, $C_5$-$C_{12}$cycloalkyl, phenyl or —CH$_2$—COO—$C_{12}$-$C_{20}$alkyl, X and a are as defined above, $X_1$ is —O—, —S—, —NH— or —N$R_{14}$—, $X_2$ is a direct bond, —CH$_2$—, >CH—CH$_3$ or —S— and $X_3$ is —O—, —S—, —NH— or —N$R_{19}$—, b is 3 to 5, c is 0 to 2, d is 0 or 1, e is 2 to 10 and f is 2 to 6;

or A, when n=2, is

—X'—C$_g$H$_{2g}$—X'—, 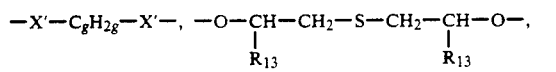

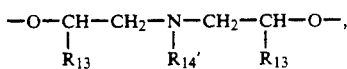

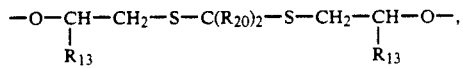

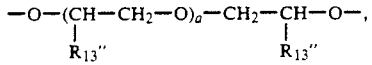

—OCH$_2$CH=CHCH$_2$O—, —OCH$_2$C≡CCH$_2$O—,

-continued

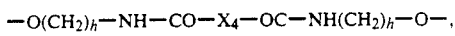

—NH(CH$_2$)$_2$—X(CH$_2$)$_2$—O—,

—NH(CH$_2$CH$_2$NH)$_f$—CH$_2$CH$_2$NH—,

—NH(CH$_2$CH$_2$CH$_2$NH)$_f$CH$_2$CH$_2$CH$_2$NH—,

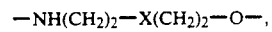

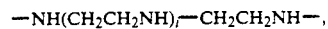

—NH—NH—, —NH—NH—CO—X$_4$—OC—NH—NH—,

—NH—N=CH—X$_5$—CH=N—NH—, —C$_a$H$_{2a}$—,

—(CH$_2$)$_m$—X$_1$—(CH$_2$)$_m$—, phenylene,

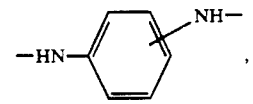

—C$_p$H$_{2p}$—CO—X—C$_g$H$_{2g}$—X—OC—C$_p$H$_{2p}$—,

—(CH$_2$)$_k$—O—CO—X$_4$—CO—O—(CH$_2$)$_k$—,

—CH=CH—CO—X—C$_g$H$_{2g}$—X—OC—CH=CH—,

—CH(OH)CH$_2$—, —CH(OH)CH(OH)—, 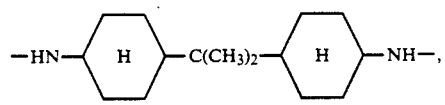

—CH=CH—, —CH($R_{21}$)— or —CH$_2$CH$_2$— 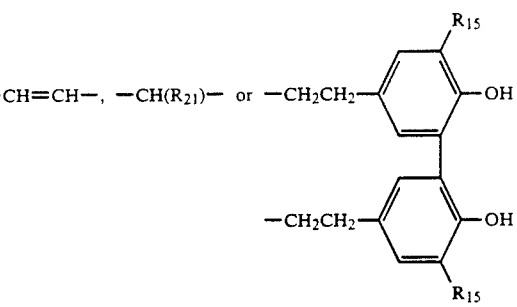

where X, $R_{13}$, $R_{15}$, a and f are as defined above, the X' independently of one another are —O— or —NH—, $R_{13}''$ is hydrogen or methyl and, if a=zero, can also be $C_2$-$C_{18}$alkyl or phenyl, $R_{14}'$ can have the same definition as $R_{14}$ or is hydrogen, the $R_{20}$ independently of one another are hydrogen, $C_1$-$C_{20}$alkyl, phenyl or together are a 5-12-membered cycloaliphatic ring, $R_{21}$ is $C_5$-$C_{12}$cycloalkyl, phenyl-$C_1$-$C_4$alkyl, phenyl or

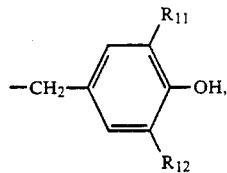

g is 2 to 12, h is 2 to 6, i is 1 to 5, k is 3 to 5, m is 1 or 2 and p is 1 to 10, $X_4$ is —$C_aH_{2a}$—, phenylene or —CH=CH— and $X_5$ is a direct bond, —$(CH_2)_3$— or —$C(CH_3)_2$—S—S—$C(CH_3)_2$—;
or A, when n=3, is

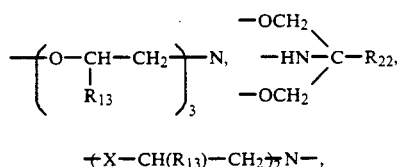

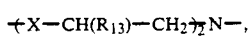

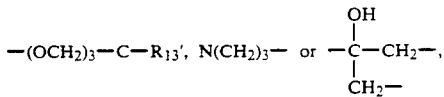

where $R_{13}$ and $R_{13}'$ are as defined above and $R_{22}$ is methyl or ethyl;
or A, when n=4, is

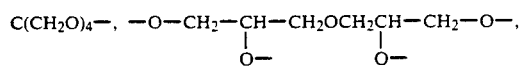

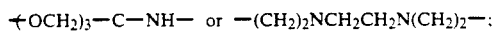

or A, when n=5, is

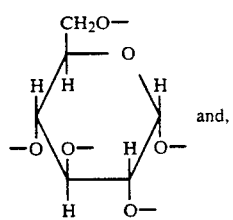

A, when n=6, is

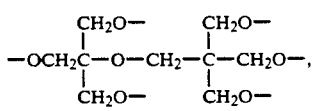

and with the proviso that, when component (a) is an unsaturated polyester and when n is 1 in formula I of component (b), then $R_4$ is hydrogen.

2. A composition according to claim 1, in which R and $R_1$ independently of one another are hydrogen, $C_1$-$C_4$alkyl, $C_1$-$C_4$alkoxy or halogen and $R_2$ and $R_3$ are hydrogen.

3. A composition according to claim 1, in which R is hydrogen, $C_1$-$C_4$alkyl, $C_1$-$C_4$alkoxy or chlorine, and $R_1$, $R_2$ and $R_3$ are hydrogen.

4. A composition according to claim 1, in which R is hydrogen, $C_1$-$C_4$alkyl, $C_1$-$C_4$alkoxy or chlorine, $R_1$, $R_2$, $R_3$ and $R_4$ are hydrogen, n is 1 or 2, A, if n=1, is —$OR_5$, —$NHR_6$, —NH—NH—$R_8$, —NH—N=CH—$R_{17}$, $C_1$-$C_{17}$alkyl,

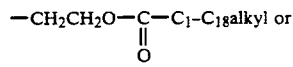

—$(CH_2)_pCO$—X—$R_{10}$, —$CH_2$—$X_1$—$C_1$-$C_{18}$alkyl,

—$(CH_2)_b$—O—C—$R_{10}'$, —$(CH_2)_b$—OH,
               ‖
               O

—CH$_2$CH$_2$—[phenyl with $R_{15}'$, OH, tert-butyl] or

—CH$_2$C(CH$_3$)—{[phenyl with OH, t-butyl]}$_2$, $R_{10}$ is hydrogen, $C_1$-$C_{18}$alkyl, $C_2$-$C_{18}$alkenyl, cyclohexyl, methylcyclohexyl or benzyl and $R_{10}'$ is $C_1$-$C_{17}$alkyl, $C_2$-$C_{17}$alkenyl or phenyl, $R_5$ is $C_1$-$C_{18}$alkyl, $C_2$-$C_{18}$alkenyl, cyclohexyl, methylcyclohexyl, benzyl, —CH—CH$_2$—X$_1$—R$_{10}''$ or [biphenyl with $R_{15}'$, $X_2$, HO, $R_{15}'$],
  |
  R$_{13}$ in which $R_{10}''$ is hydrogen, $C_1$-$C_{18}$alkyl or $C_2$-$C_{18}$alkenyl and the $R_{15}'$ independently of one another are methyl or tert-butyl, $R_6$ is $C_1$-$C_{18}$alkyl, $C_2$-$C_{18}$alkenyl, cyclohexyl, methylcyclohexyl, benzyl, —CH$_2$CH$_2$OH, —CH$_2$CH$_2$O—C—$C_1$-$C_{18}$alkyl or
         ‖
         O —CH$_2$CH$_2$O—C—$C_2$-$C_{18}$alkenyl, $R_8$ is hydrogen,
         ‖
         O $C_1$-$C_{12}$alkyl, —CO—$C_1$-$C_{18}$alkyl or —CO—$C_2$-$C_{18}$alkenyl, $R_{17}$ is $C_1$-$C_{11}$alkyl, $C_2$-$C_{11}$alkenyl, —$(CH_2)_m$—S—$C_1$-$C_{18}$alkyl or —$(CH_2)_m$—P—$(C_1$-$C_8$alkoxy)$_2$;
                                              ‖
                                              O or A, if n = 2, is —O—$(CH_2)_g$—O—, —NH—$(CH_2)_g$—NH—,

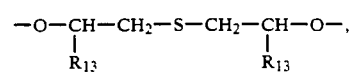

-continued

—O—CH(R13)—CH2—NH—CH2CH(R13)—O—,

—O—(CH(R13)—CH2O)a'—CH2CH(R13)—O— where a' is zero to 5 or

—OCH2—C(CH3)2CH2—O—,

—NHCH2CH2—X—CH2CH2O—,

—NH(CH2CH2NH)f—CH2CH2NH—,

—NH(CH2CH2CH2NH)f—CH2CH2CH2—NH—,

—NH—C(CH3)2—CH2O—,

—NHCH2CH2OC(O)(CH2)aC(O)OCH2CH2NH—,

—NH—NH—C(O)(CH2)aC(O)—NH—NH—,

—NH—N=CH—X5—CH=N—NH—, —(CH2)p—, phenylene,

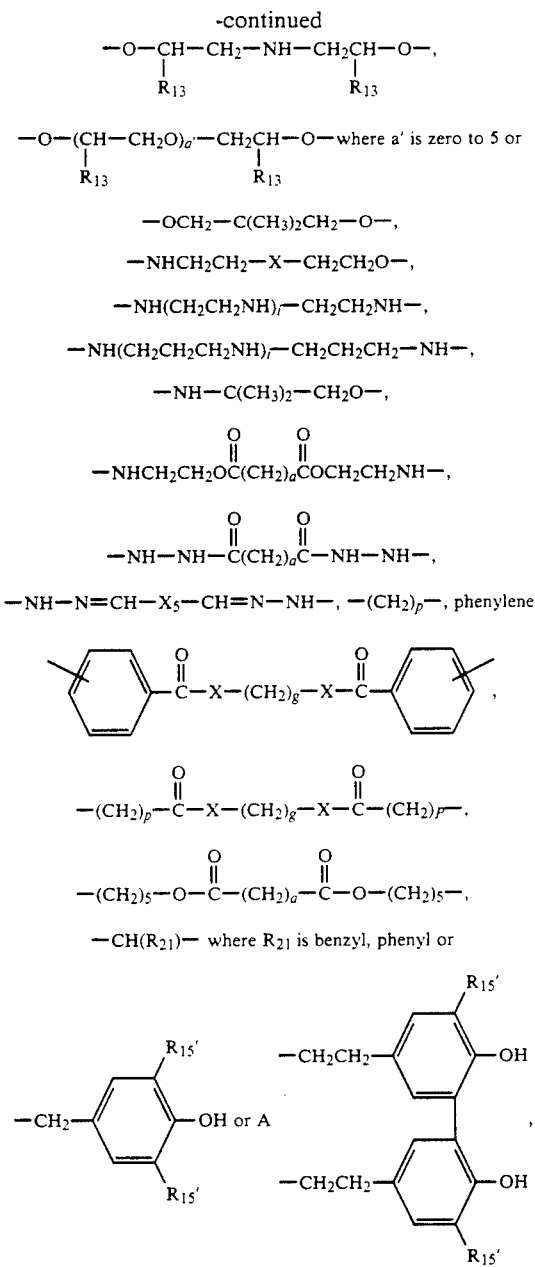

—(CH2)5—O—C(O)—(CH2)a—C(O)—O—(CH2)5—,

—CH(R21)— where R21 is benzyl, phenyl or and a, b, g, i, m, p, X, X1, X2, X5 and R13 are as defined in claim 1.

5. A composition according to claim 1, in which R is hydrogen, chlorine, methyl or methoxy and R1, R2, R3 and R4 are hydrogen, n is 1 or 2, A, if n=1, is —OR5, —NHR6, —NH—NH—R8, —NH—N=CH—R17, C1-C17alkyl, —(CH2)p—COOH, —(CH2)p—C(O)—O—C1-C18alkyl, —(CH2)bOH, —(CH2)b—OCO—C1-C18alkyl, —CH2—S—C1-C18alkyl, 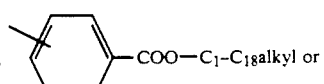 —COO—C1-C18alkyl or -continued

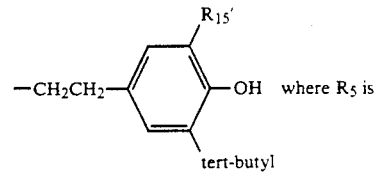 where R5 is tert-butyl

C1-C18alkyl, cyclohexyl, methylcyclohexyl, benzyl or

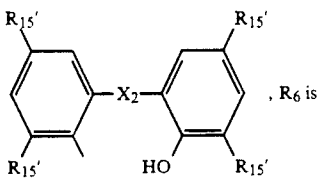, R6 is

C1-C18alkyl, cyclohexyl, benzyl, —(CH2)f—OH or

—CH2CH2O—CO—C1-C18alkyl, R8 is hydrogen, —CO—C1-C18alkyl or —COCH=CH2, the R15' independently of one another are methyl or tert-butyl, R17 is C1-C11alkyl, —(CH2)m—S—C1-C18alkyl or —(CH2)m—P(O)—(C1-C4alkoxy)2, or A, if n = 2, is —O—(CH2)g—O—, —NH—(CH2)g—NH—, —OCH2CH2SCH2CH2O—, —O(CH2CH2O)c—CH2CH2—O—,

—OCH2C(CH3)2CH2O—, —NHCH2CH2OCH2CH2O—,

—NHCH2CH2OC(O)(CH2)aC(O)OCH2CH2NH—,

—NH—NH—C(O)(CH2)aC(O)—NH—NH—,

—NH—N=CH—C(CH3)2—S—S—C(CH3)2—CH=N—NH—, phenylene or —(CH2)p—, where a, b, c, f, g, m, p and X2 are as defined in claim 1.

6. A composition according to claim 1, in which R is hydrogen, chlorine, methyl or methoxy R1, R2, R3 and R4 are hydrogen, n is 1 or 2, A, if n=1, is —OR5, —NHR6, —NH—NH—R8, —NH—N=CH—R17, C8-C17alkyl, —(CH2)p'—CO—O—C8-C18alkyl where p'=2 to 6, —(CH2)b—OH, —(CH2)b—OCO—C8-C18alkyl, —CH2—S—C8-C18alkyl,

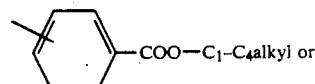—COO—C1-C4alkyl or

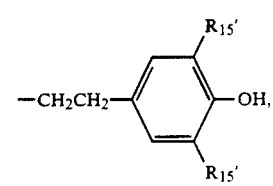

$R_5$ is $C_8$-$C_{18}$alkyl or

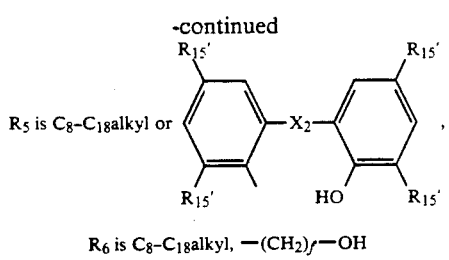

$R_6$ is $C_8$-$C_{18}$alkyl, —(CH$_2$)$_f$—OH where f' =2 or 3 or —CH$_2$CH$_2$OCO—C$_8$-C$_{18}$alkyl, R$_8$ is —CO—C$_8$-C$_{18}$alkyl or —COCH═CH$_2$, R$_{17}$ is C$_8$-C$_{11}$alkyl, (CH$_2$)$_m$—S—C$_8$-C$_{18}$alkyl or

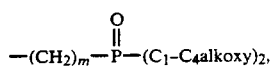

or A, if n=2, is —O(CH$_2$)$_g$O—, —NH(CH$_2$)$_g$NH—, —OCH$_2$CH$_2$SCH$_2$CH$_2$O—, —O(CH$_2$CH$_2$O)$_c$CH$_2$CH$_2$O—, —OCH$_2$C(CH$_3$)$_2$CH$_2$O—, —NHCH$_2$CH$_2$OCH$_2$CH$_2$O—, —NHCH$_2$CH$_2$OCO—(CH$_2$)$_{a'}$—OCOCH$_2$CH$_2$NH— or —NH—NHCO—(CH$_2$)$_{a'}$—CONH—NH— where a''=2 to 8, is —NH—N═CH—C(CH$_3$)$_2$—S—S—C(CH$_3$)$_2$—CH═N—NH(CH$_2$)$_{p''}$—where p''=5-10 or phenylene, b is 3 to 5, X$_2$ is a direct bond or >CH—CH$_3$, the R$_{15}'$ independently of one another are methyl or tert-butyl and c, g and m are as defined in claim 1.

7. A composition according to claim 1, in which R, R$_1$, R$_2$, R$_3$ and R$_4$ are hydrogen, n is 1 or 2, A, if n=1, is C$_8$-C$_{17}$alkyl, —OR$_5$, —NHR$_6$ or —NH—NH—CO—C$_8$-C$_{17}$alkyl, R$_5$ and R$_6$ independently of one another are C$_8$-C$_{18}$alkyl, or A, if n=2, is —O(CH$_2$)$_g$—O—, —NH(CH$_2$)$_g$NH—, —OCH$_2$C(CH$_3$)$_2$CH$_2$O—, —NH—NHCO—CH$_2$CH$_2$—OCNH—NH—, —(CH$_2$)$_{p''}$— where p''=5 to 10 or phenylene, where g is as defined in claim 1.

8. A composition according to claim 1, comprising a compound of the formula Ia

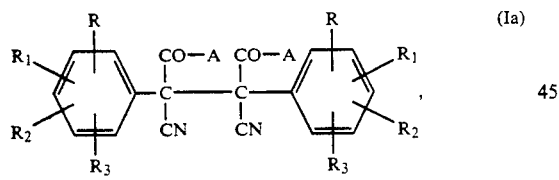

in which R is hydrogen, C$_1$-C$_4$alkyl, C$_1$-C$_4$alkoxy or chlorine, R$_1$, R$_2$ and R$_3$ are hydrogen and A is —OC$_1$-C$_{18}$alkyl.

9. A composition according to claim 8, in which R, R$_1$, R$_2$ and R$_3$ are hydrogen and A is —OC$_1$-C$_4$alkyl.

10. A composition according to claim 1, in which the organic material is a lubricant, a metal processing fluid, a hydraulic fluid or a natural, semi-synthetic or synthetic polymer.

11. A composition according to claim 1, in which the organic material is a lubricant, a halogen-free thermoplastic or an elastomer.

12. A composition according to claim 1, in which the organic material is a halogen-free polyolefin.

13. A method for stabilizing a polymer, functional fluid or lubricant as defined in claim 1, which comprises adding an effective stabilizing amount of a compound of formula I according to claim 1 to said polymer, functional fluid or lubricant.

14. A compound of formula Ib

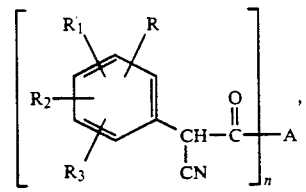

in which R is hydrogen, —OH, halogen, C$_1$-C$_{20}$alkyl, C$_2$-C$_{20}$alkenyl, C$_5$-C$_{12}$cycloalkyl, C$_1$-C$_4$alkyl-C$_5$-C$_{12}$cycloalkyl, phenyl, naphthyl, C$_1$-C$_{20}$alkoxy, phenyloxy, naphthyloxy, —S—C$_1$-C$_{20}$alkyl, —S—phenyl, —S—naphthyl, —O—CO—C$_1$-C$_{20}$alkyl, —O—CO—phenyl, —O—CO—naphthyl, —COOH, —COO—C$_1$-C$_{20}$alkyl, —COO—C$_2$-C$_{20}$alkenyl, —COO—phenyl, —COO—naphthyl, —CONR'R'', —CO—C$_1$-C$_{20}$alkyl, —CO—phenyl, —CO—naphthyl, —NHCO—C$_1$-C$_{20}$alkyl, —NHCO—C$_2$-C$_{20}$alkenyl, —NHCO—phenyl or —NHCO—naphthyl, R$_1$ can have the same definition as R, R$_2$ is hydrogen, halogen or C$_1$-C$_4$alkyl and R$_3$ is hydrogen or halogen, or two radicals R, R$_1$, R$_2$ or R$_3$ bonded to one another in the ortho-position together form tetramethylene or —CH═CH—CH═CH—, where the remaining two of R, R$_1$, R$_2$ and R$_3$ are hydrogen, R' and R'' independently of one another are hydrogen, C$_1$-C$_{20}$alkyl, C$_2$-C$_{20}$alkenyl, phenyl or naphthyl or, together with the bonding N atom, form a 5- or 6-membered heterocyclic ring, a is zero to 10, n is 1 to 6, X is —O— or —NH—, A, when n=1, is —OR$_5$, —NR$_6$R$_7$, —NHNR$_8$R$_9$, C$_1$-C$_{30}$alkyl, C$_2$-C$_{30}$alkenyl, C$_5$-C$_{12}$cycloalkyl, C$_1$-C$_4$alkyl-C$_5$-C$_{12}$cycloalkyl,

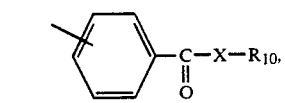

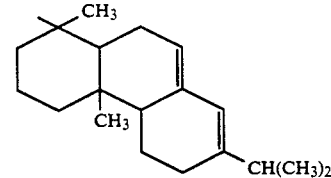

or the corresponding dihydro or tetrahydro derivative, —C$_a$H$_{2a}$—CO—X—R$_{10}$, —C$_b$H$_{2b}$—OCO—R$_{10}$, —C$_b$H$_{2b}$—OH,

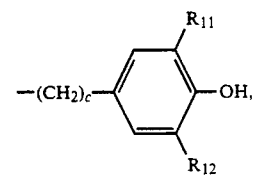

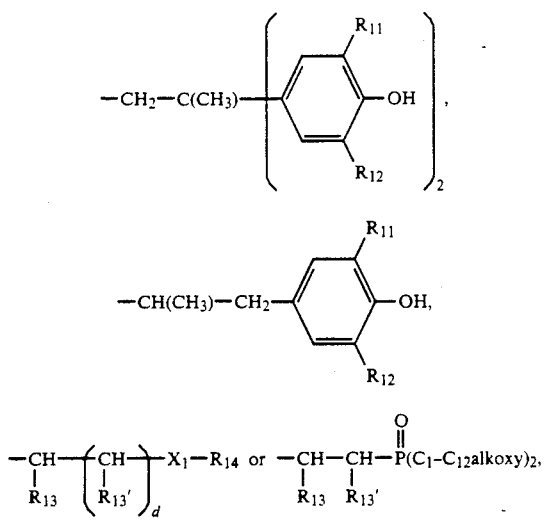

where
R$_5$ is C$_8$–C$_{18}$alkyl, C$_2$–C$_{30}$alkenyl, —C$_5$–C$_{12}$cycloalkyl, C$_1$–C$_4$alkyl-C$_5$–C$_{12}$cycloalkyl, phenyl-C$_1$–C$_4$alkyl, phenyl, naphthyl, biphenyl, the radical of a terpene alcohol or a radical of the formula

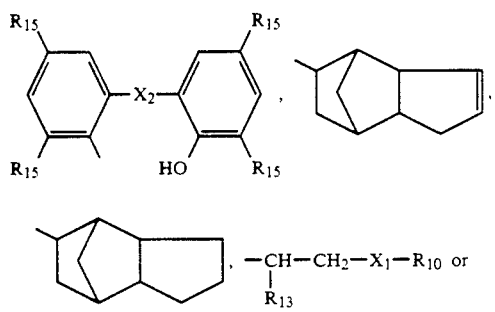

R$_6$ and R$_7$ independently of one another are C$_1$–C$_4$alkyl-C$_5$–C$_{12}$cycloalkyl, —CH$_2$—CH(R$_{13}$)—X—R$_{16}$ or —CH$_2$C(CH$_2$—O—R$_{16}$)$_3$,
R$_7$ is also hydrogen, or R$_6$, when R$_7$=hydrogen, can also be —(CH$_2$)$_f$—X—R$_{16}$,
R$_8$ is C$_1$–C$_{20}$alkyl, phenyl, —CO—C$_1$–C$_{20}$alkyl, —CO—C$_2$–C$_{18}$alkenyl, —CO-phenyl or —CO-naphthyl,
R$_9$ is hydrogen, or R$_9$ together with R$_8$ is =CH—R$_{17}$,
R$_{10}$ is hydrogen, C$_8$–C$_{20}$alkyl, C$_2$–C$_{20}$alkenyl, C$_5$–C$_{12}$cycloalkyl, phenyl-C$_1$–C$_4$alkyl, phenyl, naphthyl, —CO—C$_1$–C$_{20}$alkyl, —CO-phenyl, —CO-naphthyl or

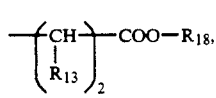

R$_{11}$ and R$_{12}$ independently of one another are hydrogen, C$_1$–C$_4$alkyl, cyclohexyl or phenyl, R$_{13}$ is hydrogen or methyl and R$_{13}'$ is hydrogen, methyl or phenyl, R$_{14}$ is C$_1$–C$_{20}$alkyl, C$_2$–C$_{20}$alkenyl, C$_5$–C$_{12}$cycloalkyl, phenyl-C$_1$–C$_4$alkyl, phenyl or naphthyl, the R$_{15}$ independently of one another are C$_1$–C$_4$alkyl, R$_{16}$ is hydrogen, —CO—C$_1$–C$_{20}$alkyl, —CO—C$_2$–C$_{20}$alkenyl, —CO-phenyl or —CO-naphthyl, R$_{17}$ is C$_1$–C$_{20}$alkyl, C$_2$–C$_{20}$alkenyl, C$_5$–C$_{12}$cycloalkyl, phenyl, naphthyl, 2-furyl,

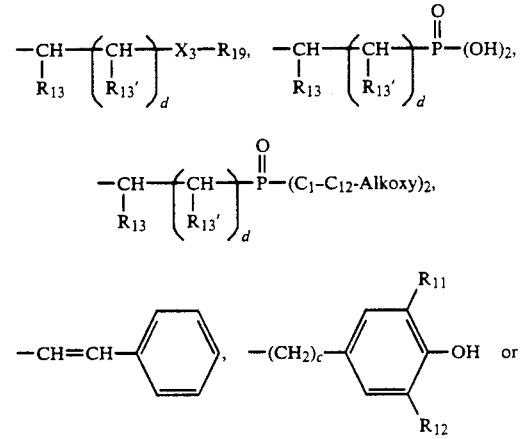

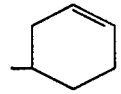

R$_{18}$ is hydrogen, C$_1$–C$_{20}$alkyl, C$_2$–C$_{20}$alkenyl, R$_{19}$ is C$_1$–C$_{20}$alkyl, C$_5$–C$_{12}$cycloalkyl, phenyl or —CH$_2$—COO—C$_{12}$–C$_{20}$alkyl, X and a are as defined above, X$_1$ is —O—, —S—, —NH— or —NR$_{14}$—, X$_2$ is a direct bond, —CH$_2$—, >CH—CH$_3$ or —S— and X$_3$ is —O—, —S—, —NH— or —NR$_{19}$—, b is 3 to 5, c is 0 to 2, d is 0 or 1, e is 2 to 10 and f is 2 to 6; with the proviso that A is not —OC$_1$–C$_{12}$alkyl, —NH$_2$, —NH-methyl, —NH-cyclohexyl, —NH-phenyl,

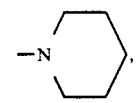

—NH—NH$_2$, C$_1$–C$_7$alkyl, —CH$_2$N(CH$_3$)$_2$, —CH$_2$N(methyl)(phenyl) or —C$_{a''}$H$_{2a''}$—CO—O—R$_{10'}$ where a''=2 or 4 and R$_{10'}$=hydrogen, methyl or ethyl, if R is hydrogen, chlorine, methyl or methoxy and R$_1$, R$_2$ and R$_3$ are hydrogen;
or A, when n=2, is

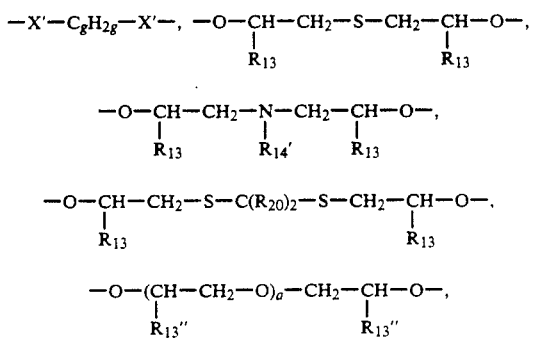

-continued

—OCH₂CH=CHCH₂O—, —OCH₂C≡CCH₂O—,

—O(CH₂)ₕ—NH—CO—X₄—OC—NH(CH₂)ₕ—O—,

—NH(CH₂)₂—X(CH₂)₂—O—,

—NH(CH₂CH₂NH)ᵢ—CH₂CH₂NH—,

—NH(CH₂CH₂CH₂NH)ᵢCH₂CH₂CH₂NH—,

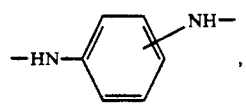

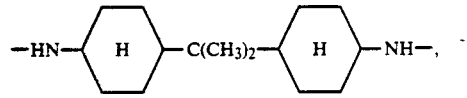

—NH(CH₂)ₕ—O—CO—X₄—OC—O—(CH₂)ₕ—NH—,

—NH—NH—, —NH—NH—CO—X₄—OC—NH—NH—,

—NH—N=CH—X₅—CH=N—NH—, —CₐH₂ₐ—,

—(CH₂)ₘ—X₁—(CH₂)ₘ—, phenylene,

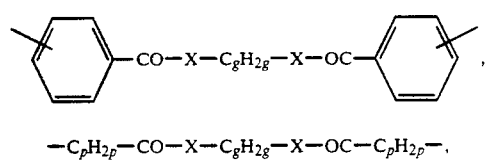

—CₚH₂ₚ—CO—X—C₈H₂ g—X—OC—CₚH₂ₚ—,

—(CH₂)ₖ—O—CO—X₄—CO—O—(CH₂)ₖ—,

—CH=CH—CO—X—C₈H₂ g—X—OC—CH=CH—,

—CH(OH)CH₂—, —CH(OH)CH(OH)—, —CH₂—C(=CH₂)—,

—CH=CH—, —CH(R₂₁)— or —CH₂CH₂—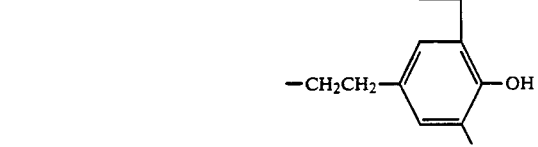

where X, R₁₃, R₁₅, a and f are as defined above, the X′ independently of one another are —O— or —NH—, R₁₃″ is hydrogen or methyl and, if a=-zero, can also be C₂-C₁₈alkyl or phenyl, R₁₄′ can have the same definition as R₁₄ or is hydrogen, the R₂₀ independently of one another are hydrogen, C₁-C₂₀alkyl, phenyl or together are a 5-12-membered cycloaliphatic ring, R₂₁ is C₅-C₁₂cycloalkyl, phenyl-C₁-C₄alkyl, phenyl or

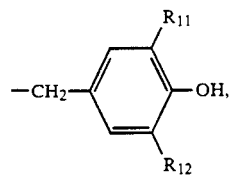

g is 2 to 12, h is 2 to 6, i is 1 to 5, k is 3 to 5, m is 1 or 2 and p is 1 to 10, X₄ is —CₐH₂ₐ—, phenylene or —CH=CH— and X₅ is a direct bond, —(CH₂)₃— or —C(CH₃)₂—S—S—C(CH₃)₂—;
or A, when n=3, is

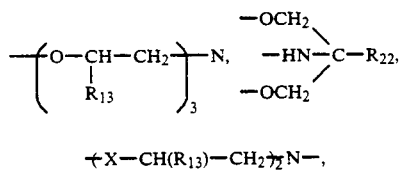

—(OCH₂)₃—C—R₁₃′, N(CH₂)₃— or —C(OH)(CH₂—)CH₂—, where R₁₃ and R₁₃′ are as defined above and R₂₂ is methyl or ethyl;
or A, when n=4,

C(CH₂O)₄—, —O—CH₂—CH(O—)—CH₂OCH₂CH(O—)—CH₂—O—, (OCH₂)₃—C—NH— or —(CH₂)₂NCH₂CH₂N(CH₂)₂—;

or A, when n=5, is

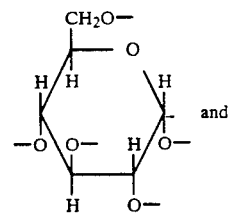
and or A, when n=6, is

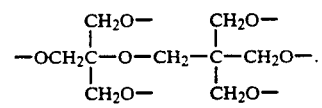

15. A compound according to claim 14, in which R and R₁ independently of one another are hydrogen, C₁-C₄alkyl, C₁-C₄alkoxy or halogen and R₂ and R₃ are hydrogen.

16. A compound according to claim 14, in which R is hydrogen, C₁-C₄alkyl, C₁-C₄alkoxy or chlorine, and R₁, R₂ and R₃ are hydrogen.

17. A compound according to claim 14, in which R is hydrogen, C₁-C₄alkyl, C₁-C₄alkoxy or chlorine, R₁, R₂ and R₃ are hydrogen, n is 1 or 2, A, if n=1, is —OR₅, —NHR₆, —NH—NH—$R_8$, —NH—N=CH—$R_{17}$, $C_1$-$C_{17}$alkyl, $C_2$-$C_{17}$alkenyl, 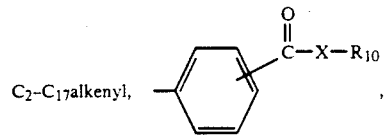

—$(CH_2)_p$CO—X—$R_{10}$, —$CH_2$—$X_1$—$C_1$-$C_{18}$alkyl,

—$(CH_2)_b$—O—C(=O)—$R_{10}'$, —$(CH_2)_b$—OH,

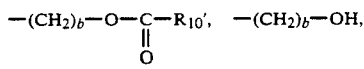

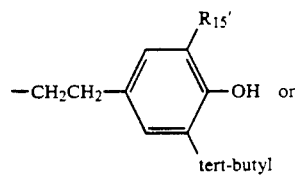

$R_{10}$ is hydrogen, $C_8$-$C_{18}$alkyl, $C_2$-$C_{18}$alkenyl, cyclohexyl, methylcyclohexyl or benzyl and $R_{10}'$ is $C_1$-$C_{17}$alkyl, $C_2$-$C_{17}$alkenyl or phenyl, $R_5$ is $C_8$-$C_{18}$alkyl, $C_2$-$C_{18}$alkenyl, cyclohexyl, methylcyclohexyl, benzyl,

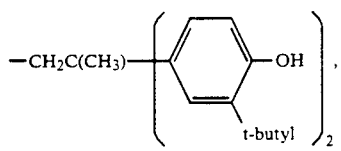

in which $R_{10}''$ is hydrogen, $C_1$-$C_{18}$alkyl or $C_2$-$C_{18}$alkenyl and the $R_{15}'$ independently of one another are methyl or tert-butyl, $R_6$ is methylcyclohexyl, —$CH_2CH_2OH$,

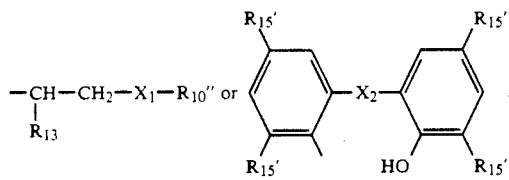

$R_8$ is $C_1$-$C_{12}$alkyl, —CO—$C_1$-$C_{18}$alkyl or —CO—$C_2$-$C_{18}$alkenyl, $R_{17}$ is $C_1$-$C_{11}$alkyl, $C_2$-$C_{11}$alkenyl, —$(CH_2)_m$—S—$C_1$-$C_{18}$alkyl or

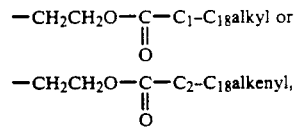

or A, if n = 2, is —O—$(CH_2)_g$—O—, —NH—$(CH_2)_g$—NH—,

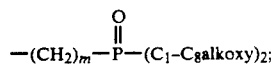

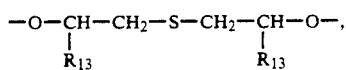

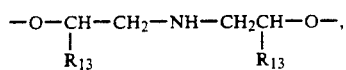

-continued

—O—(CH—$CH_2O)_{a'}$—$CH_2CH$—O— where $a'$ = zero to 5, or
  |                            |
  $R_{13}$                     $R_{13}$

—$OCH_2$—$C(CH_3)_2CH_2$—O—,

—$NHCH_2CH_2$—X—$CH_2CH_2O$—,

—$NH(CH_2CH_2NH)_i$—$CH_2CH_2NH$—,

—$NH(CH_2CH_2CH_2NH)_i$—$CH_2CH_2CH_2$—NH—,

—NH—$C(CH_3)_2$—$CH_2O$—,

—$NHCH_2CH_2OC(=O)(CH_2)_a COCH_2CH_2NH$—,

—NH—NH—$C(=O)(CH_2)_a C(=O)$—NH—NH—,

—NH—N=CH—$X_5$—CH=N—NH—, —$(CH_2)_p$—,

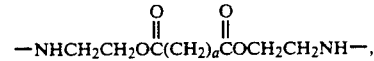

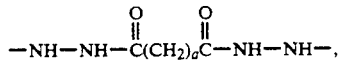

—$(CH_2)_5$—O—C(=O)—$(CH_2)_a$—C(=O)—O—$(CH_2)_5$—, —CH($R_{21}$)— where $R_{21}$ = benzyl, phenyl or 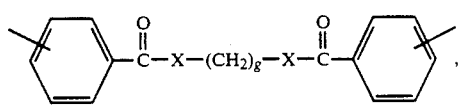 or A is

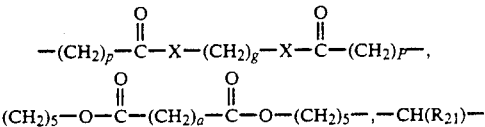

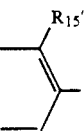

and a, b, g, i, m, p, X, $X_1$, $X_2$, $X_5$ and $R_{13}$ are as defined in claim 14.

18. A compound according to claim 14, in which R is hydrogen, chlorine, methyl or methoxy and $R_1$, $R_2$ and $R_3$ are hydrogen, n is 1 or 2, A, if n=1, is —$OR_5$, —$NHR_6$, —NH—NH—$R_8$, —NH—N=CH—$R_{17}$, $C_8$-$C_{17}$alkyl, —$(CH_2)_p$—COOH, —$(CH_2)_p$—C(=O)—O—$C_8$-$C_{18}$alkyl, —$(CH_2)_b$OH, —$(CH_2)_b$—OCO—$C_1$-$C_{18}$alkyl, -continued

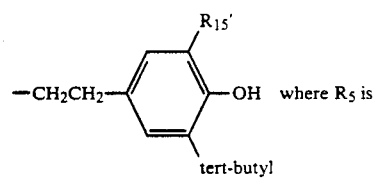 where R₅ is tert-butyl $C_{13}$-$C_{18}$alkyl, cyclohexyl, methylcyclohexyl, benzyl or

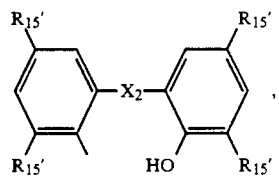, $R_6$ is —$(CH_2)_f$—OH or —$CH_2CH_2O$—CO—$C_1$-$C_{18}$alkyl, $R_8$ is —CO—$C_1$-$C_{18}$alkyl or —COCH=$CH_2$, the $R_{15}'$ independently of one another are methyl or tert-butyl, $R_{17}$ is $C_1$-$C_{11}$alkyl, —$(CH_2)_m$—S—$C_1$-$C_{18}$alkyl or

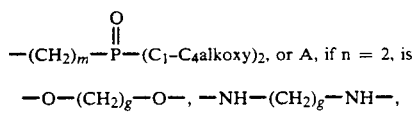, or A, if n = 2, is

—O—$(CH_2)_g$—O—, —NH—$(CH_2)_g$—NH—,

—OCH$_2$CH$_2$SCH$_2$CH$_2$O—, —O(CH$_2$CH$_2$O)$_c$—CH$_2$CH$_2$—O—,

—OCH$_2$C(CH$_3$)$_2$CH$_2$O—, —NHCH$_2$CH$_2$OCH$_2$CH$_2$O—,

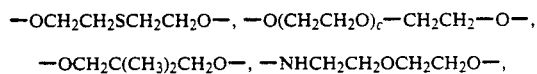,

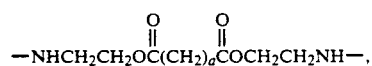,

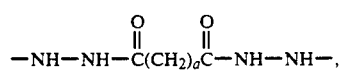 or

—$(CH_2)_p$—, where a, b, c, f, g, m, p and $X_2$ are as defined in claim 14.

19. A compound according to claim 14, in which R is hydrogen, chlorine, methyl or methoxy $R_1$, $R_2$ and $R_3$ are hydrogen, n is 1 or 2, A, if n=1, is —OR$_5$, —NHR$_6$, —NH—NH—R$_8$, —NH—N=CH—R$_{17}$, $C_8$-$C_{17}$alkyl, —(CH$_2$)$_{p'}$—CO—O—$C_8$-$C_{18}$alkyl where p'=2 to 6, —$(CH_2)_b$—OH, —$(CH_2)_b$—OCO—$C_8$-$C_{18}$alkyl, —CH$_2$—S—$C_8$-$C_{18}$alkyl,

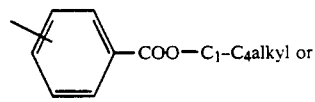 or

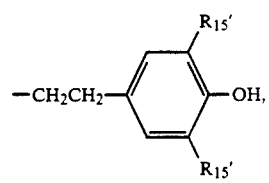, $R_5$ is $C_{13}$-$C_{18}$alkyl or 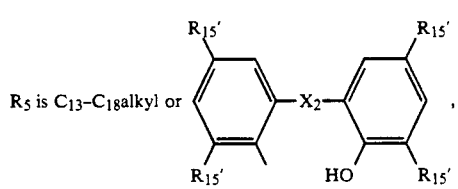, $R_6$ is —$(CH_2)_f$—OH where f"=2 or 3 or —CH$_2$CH$_2$OCO—$C_8$-$C_{18}$alkyl, $R_8$ is —CO—$C_8$-$C_{18}$alkyl or —COCH=CH$_2$, $R_{17}$ is $C_8$-$C_{11}$alkyl, $(CH_2)_m$—S—$C_8$-$C_{18}$alkyl or

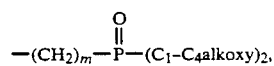, or A, if n=2, is —O(CH$_2$)$_g$O—, —NH(CH$_2$)$_g$NH—, —OCH$_2$CH$_2$SCH$_2$CH$_2$O—, —O(CH$_2$CH$_2$O)$_c$CH$_2$C-H$_2$O—, —OCH$_2$C(CH$_3$)$_2$CH$_2$O—, —NHCH$_2$C-H$_2$OCH$_2$CH$_2$O—, —NHCH$_2$CH$_2$OCO—(CH$_2$)$_{a''}$-—OCOCH$_2$CH$_2$NH— or —NH—NHCO—(CH$_2$)$_{a''}$-—CONH—NH— where a"=2 to 8, —NH—N=CH—C(CH$_3$)$_2$—S—S—C(CH$_3$)$_2$—CH=N—NH— or —(CH$_2$)$_{p''}$ where p"=5-10, b is 3 to 5, $X_2$ is a direct bond or >CH—CH$_3$, the $R_{15}'$ independently of one another are methyl or tert-butyl and c, g and m are as defined in claim 14.

20. A compound according to claim 14, in which R, $R_1$, $R_2$ and $R_3$ are hydrogen, n is 1 or 2, A, if n=1, is $C_8$-$C_{17}$alkyl, —OR$_5$, —NHR$_6$ or —NH—N-H—CO—$C_8$-$C_{17}$alkyl, and R$_5$ is $C_{13}$-$C_{18}$alkyl and, or A, if n=2, is —O(CH$_2$)$_g$—O—, —NH(CH$_2$)$_g$NH—, —OCH$_2$C(CH$_3$)$_2$CH$_2$O—, —NH—NHCO—CH$_2$C-H$_2$—OCNH—NH— or —(CH$_2$)$_{p''}$— where p"=5 to 10, where g is as defined in claim 14.

* * * * *